(12) United States Patent
Li et al.

(10) Patent No.: US 9,414,926 B2
(45) Date of Patent: *Aug. 16, 2016

(54) IMPLANT FOR RESTORING NORMAL RANGE FLEXION AND KINEMATICS OF THE KNEE

(71) Applicant: The General Hospital Corporation, Boston, MA (US)

(72) Inventors: Guoan Li, Milton, MA (US); Harry E. Rubash, Weston, MA (US); Kartik Mangudi Varadarajan, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/550,755

(22) Filed: Nov. 21, 2014

(65) Prior Publication Data

US 2015/0088264 A1 Mar. 26, 2015

Related U.S. Application Data

(63) Continuation of application No. 13/491,126, filed on Jun. 7, 2012, now Pat. No. 8,911,502, which is a continuation of application No. PCT/US2010/059387, filed on Dec. 8, 2010.

(60) Provisional application No. 61/268,000, filed on Dec. 9, 2009.

(51) Int. Cl.
*A61F 2/38* (2006.01)

(52) U.S. Cl.
CPC . *A61F 2/389* (2013.01); *A61F 2/38* (2013.01); *A61F 2/3836* (2013.01); *A61F 2230/0063* (2013.01)

(58) Field of Classification Search
CPC ......... A61F 2/38; A61F 2/3836; A61F 2/389; A61F 2002/2892; A61F 2002/30317; A61F 2002/30322; A61F 2002/30326; A61F 2002/30319
See application file for complete search history.

(56) References Cited

U.S. PATENT DOCUMENTS 4,963,152 A 10/1990 Hofmann et al.
5,549,688 A 8/1996 Ries et al.
(Continued)

OTHER PUBLICATIONS

Caradarajan et al., "Changes in Tibiofemoral Joint Space following Total Knee Arthroplasty during Weightbearing Knee Motion", Proceedings of the ASME Summer Bioengineering Conference, Lake Tahoe, CA, Jun. 2009.

(Continued)

*Primary Examiner* — David Isabella
*Assistant Examiner* — Dinah Baria
(74) *Attorney, Agent, or Firm* — Quarles & Brady LLP

(57) ABSTRACT

Embodiments of the invention provide knee prostheses which more faithfully and closely replicate the function, anatomy and physiology of the normal human knee yielding a number of advantages. Among other things, such prostheses can provide an increased range of motion and function more normally particularly in extension, deep flexion and during normal gait. Knee prostheses according to various aspects of the invention recognize that during movement of the knee, particularly during flexion, the kinematics of the bones of the knee are a result of achieving equilibrium of the forces that cause motion of the knee. In addition, the shape of the articular surfaces acting in combination with forces imposed by various muscles, ligaments and tendons, determines the direction of the large contact forces.

5 Claims, 24 Drawing Sheets

(56) References Cited

U.S. PATENT DOCUMENTS

| | | |
|---|---|---|
| 5,681,354 A | 10/1997 | Eckhoff |
| 5,824,105 A | 10/1998 | Ries et al. |
| 5,964,808 A | 10/1999 | Blaha et al. |
| 7,066,963 B2 | 6/2006 | Naegerl |
| 2002/0058997 A1 | 5/2002 | O'Connor et al. |
| 2005/0096747 A1 | 5/2005 | Tuttle et al. |
| 2007/0135926 A1 | 6/2007 | Walker |
| 2008/0009950 A1 | 1/2008 | Richardson |
| 2008/0119940 A1 | 5/2008 | Otto et al. |

OTHER PUBLICATIONS

International Preliminary Report on Patentability for Application No. PCT/US2010/059387, issued Jun. 21, 2012. (6 Pages).

International Search Report and Written Opinion for Application No. PCT/US201 0/059387, issued Aug. 29, 2011. (10 Pages).

CONTOURED SUPEROPOSTERIOR LATERAL CONDYLE TO ALLOW
FOR AXIAL ROTATION FOR FEMORAL COMPONENT ABOUT A MEDIAL PIVOT

STANDARD TIBIAL BONE CUT IN
FRONTAL VIEW

STANDARD TIBIAL BONE CUT IN
SAGITTAL VIEW

IMPLANT FOR RESTORING NORMAL RANGE FLEXION AND KINEMATICS OF THE KNEE

CROSS-REFERENCE TO RELATED APPLICATIONS

The present application is a continuation of U.S. application Ser. No. 13/491,126 filed Jun. 7, 2012, which claims priority to PCT International Application No. PCT/US10/59387, filed on Dec. 8, 2010, which claims priority to U.S. Provisional Application No. 61/268,000, filed on Dec. 9, 2009 which are hereby incorporated by reference in their entireties.

STATEMENT REGARDING FEDERALLY SPONSORED RESEARCH

N/A

FIELD OF THE INVENTION

The present invention relates broadly to knee joint prostheses.

BACKGROUND OF THE INVENTION

Disease and trauma affecting the articular surfaces of the knee joint are commonly treated by surgically replacing the ends of the femur and tibia with prosthetic femoral and tibial implants, and, in some cases, replacing the patella with a patella component. Such surgeries are sometimes referred to as total knee arthroplasty (TKA). In TKA surgery, a surgeon typically affixes two prosthetic components to the patient's bone structure; a first to the patient's femur and a second to the patient's tibia. These components are typically known as the femoral component and the tibial component respectively.

The femoral component is placed on a patient's distal femur after appropriate resection of the femur. The femoral component is usually metallic, having a highly polished outer condylar articulating surface, which is commonly J-shaped. A common type of tibial component consists of a top surface (plateau) that generally conforms to the patient's resected proximal tibia. The bottom surface of the tibial component also usually includes a stem that extends at an angle to the plateau in order to extend into a surgically formed opening in the tibial intramedullary canal. Two common designs of the tibial component exist. In one design, the tibial component is monolithic (single piece) and made of plastic/polymeric material. In another design, a plastic or polymeric (often ultra high molecular weight polyethylene) tray is affixed on top of a tibial base plate which includes the stem and is usually made of metal. The top surface of the tibial component provides a surface against which the femoral component condylar portion articulates, i.e., moves in gross motion corresponding generally to the motion of the femur relative to the tibia.

While TKA is a highly successful surgical treatment option for severe knee joint disease such as osteoarthritis and rheumatoid arthritis, several studies have shown that current TKA implants do not restore the motion of the knee to the normal/healthy state, thus limiting patient function following surgery. Typically, the active (as opposed to passive when muscles are relaxed) range of knee flexion following TKA is limited to less than 115 degrees, whereas the healthy knee is capable of bending up to 160 degrees. Increased range of knee motion is required for activities like squatting and kneeling, which are particularly important for patients of certain ethnic and religious groups, as well as certain occupations and leisure activities. In addition to limited range of motion, complications, particularly of the patellofemoral joint, including chronic pain, patellar subluxation, patellar tilt, patellar dislocation and patellar component loosening have also been observed in 1-20% of TKA patients.

These limitations of TKA have in part been related to the inability of existing designs to replicate in vivo knee joint kinematics, including the kinematics of the femur relative to the tibia (tibiofemoral kinematics) and the patella relative to the femur (patellofemoral kinematics). The tibiofemoral kinematics following TKA are characterized by reduced posterior femoral translation and reduced internal tibial rotation, compared to normal knees. In addition, unexpected anterior femoral translation has been frequently noted in knees with TKA. Current TKA designs have also been shown to have abnormal patellofemoral kinematics. For example, studies have shown more superior patellofemoral contact, inconsistent patellar tracking, patellofemoral separation, and higher patellar tilt angles in TKA compared to normal knees.

Furthermore, many existing TKA designs only use kinematic information in 3 out of the 6 degrees-of-freedom, i.e., they include information regarding anteroposterior translation, internal-external rotation and flexion, but they do not include information about mediolateral translation, superoinferior translation and varus-valgus rotation. Information regarding superoinferior translation and varus-valgus rotation is particularly important to ensure that the tibiofemoral joint is not overstuffed in deep flexion, as often happens in patients receiving standard TKA. In addition, while TKA designs are beginning to incorporate kinematic features of the tibiofemoral joint, the patellofemoral joint has largely been ignored.

Accordingly, there remains a need for improved knee prostheses and methods for treating disease and trauma affecting the knee.

SUMMARY OF THE INVENTION

The present invention provides methods and devices for knee replacement. In one embodiment, a knee joint prosthesis is provided and can include a tibial component having an inferior surface and a superior surface that serves as a bearing surface for a femoral component. The superior surface can have a generally concave medial compartment configured to receive and articulate with a medial femoral condyle. In some embodiments, the medial compartment can have a generally straight configuration along a length extending from an anterior end thereof to a posterior end thereof. The tibial component can further include a generally concave lateral compartment configured to receive and articulate with a lateral femoral condyle. The lateral compartment can be curved about a medial center and can have a length extending from an anterior end thereof to a posterior end thereof that is greater than the length of the medial compartment. The tibial component can also include a central portion disposed between the medial and lateral compartments. At least one of an anterior edge and a posterior edge of the tibial component is angled relative to a line perpendicular to a tibial base of the tibial component.

While the lateral compartment can have many configurations, in one embodiment, the lateral compartment can have an anteroposterior profile that is characterized by a first, anterior arc that is concave, a second arc posterior to the first arc that is convex, and a third arc posterior to the second arc that is concave. The medial compartment can have an anteroposterior profile that is characterized by, for example, a first, anterior arc that is concave and a second, posterior arc that is concave, wherein the first and second arcs each have a different radius of curvature. The medial compartment can also include a convex posterior edge posterior to the second arc that is configured to allow stable contact with the femoral component during deep flexion. In other embodiments, the medial compartment can have an anteroposterior profile that is characterized by a first, anterior arc that is concave, a second arc posterior to the first arc that is convex, and a third arc posterior to the second arc that is concave. The medial compartment can also include a convex posterior edge posterior to the third arc and configured to allow stable contact with the femoral component during deep flexion. The lateral and medial compartments can have any relative size as needed, but in some embodiments, an anteroposterior dimension of the second, convex arc of the lateral compartment can increase in size from a medial portion of the lateral compartment to a lateral portion of the lateral compartment.

The central portion can include an anterior ramp for engaging a trochlear groove formed in the femoral component and configured to prevent abnormal posterior femoral shift. The central portion can also include a posterior asymmetric post configured to engage a cam on the femoral component and configured to induce posterior femoral translation at flexion angles greater than about 75 degrees. In some embodiments, the tibial component can be configured to mate to a resected tibia. In other embodiments, the knee prosthesis can also include a tibial base having an inferior surface configured to mate with a resected tibia and a superior surface configured to mate with the tibial component.

The knee prosthesis can further include a femoral component having opposed medial and lateral condyles, each with a bearing surface configured to articulate with the medial and lateral compartments of the tibial component. The femoral component can be configured to mate to a resected femur. The knee joint can allow flexion of up to 150 degrees flexion when implanted in a human body.

In other aspects, a knee joint prosthesis is provided and can include a femoral component configured for bearing against a tibial component. The femoral component can include medial and lateral femoral condyles, each having a generally convex inferior bearing surface configured to engage and articulate with a tibial compartment. In some embodiments, the bearing surface of the medial femoral condyle can have at least seven distinct circular arcs, each circular arc having a different radius. In addition, the bearing surface of the lateral femoral condyle can have at least six circular arcs, each circular arc having a different radius. A trochlear groove can be disposed between the medial and lateral femoral condyles.

The medial femoral condyle can have many configurations and can include a groove positioned on the bearing surface thereof between fourth and fifth circular arcs from an anteriormost first circular arc. A fourth circular arc through a seventh circular arc from an anteriormost first circular arc of the medial femoral condyle can have progressively decreasing radii. A third circular arc through a sixth circular arc from an anterior-most first circular arc of the lateral femoral condyle can have progressively decreasing radii. In one embodiment, the lateral femoral condyle can include a contoured lateral edge configured to allow unimpeded rotation of the lateral femoral condyle about a medial pivot point. The trochlear groove can include two laterally oriented circular arcs having different radii of curvature configured for engaging an anterior ramp of the tibial component to prevent abnormal posterior femoral shift.

In another embodiment, a knee joint prosthesis can have a femoral component with a central axis, medial and lateral condyles, and a trochlear groove disposed between the medial and lateral condyles. The trochlear groove can include a distal portion neutrally oriented relative to the central axis, a central portion medially oriented relative to the central axis, and a proximal portion laterally oriented relative to the central axis. The femoral component can also have a mediolateral axis and the trochlear groove can have a distal portion tilted at a medial orientation relative to the mediolateral axis, a central portion tilted at a medial orientation relative to the mediolateral axis that is greater than the medial orientation of the distal portion, and a proximal portion tilted at a medial orientation relative to the mediolateral axis that is less than the medial orientation of the distal portion.

In other aspects, a knee joint prosthesis is provided and can include a femoral component having asymmetric medial and lateral condyles and a tibial component having asymmetric medial and lateral surfaces that engage the asymmetric medial and lateral condyles. The femoral component and the tibial component can be configured to allow axial rotation of the femoral component relative to the tibial component about a medial pivot point when implanted in a body, to restore flexion up to about 150 degrees when implanted in a body, and to allow posterior translation of a femur to which the femoral component is attached.

In a further aspect, a knee joint prosthesis is provided and can include a tibial component having a generally concave medial compartment having a generally straight orientation in an anterior-posterior direction with a first length and a generally concave lateral compartment, the lateral compartment having a curved orientation in the anterior-posterior direction and having a second length. The curved lateral compartment can be configured to guide greater posterior motion of a lateral femoral condyle compared to posterior motion of a medial femoral condyle. The first length can be less than the second length.

In one embodiment, a tibial component of a knee joint prosthesis is provided and can include a lateral tibial compartment with a concave anterior region having a first length, a convex central-posterior region, and a concave posterior region having a second length. The first length can be less than the second length and the central-posterior region can increase in length in a medial to lateral direction and can be configured to allow femoral rotation about an overall medially located axis.

In another embodiment, a tibial component of a knee joint prosthesis is provided and can include a medial tibial surface with a concave anterior region having a first length, and a concave posterior region having a second length. The first length can be greater than the second length.

In one aspect, a tibial component of a knee joint prosthesis is provided and can include a medial tibial surface with a concave anterior region having a first length, a convex central region having a second length, and a concave posterior region having a third length. The first length can be greater than the second and third lengths, and the third length can be greater than the second length.

In a further aspect, a tibial component of a knee joint prosthesis is provided and can include a medial tibial surface with substantially rounded posterior edge configured to prevent impingement with femoral bone in high knee flexion and to allow stable contact with the femoral bone in deep flexion.

In still a further aspect, a tibial component of a knee joint prosthesis is provided and can include a central portion positioned between medial and lateral tibial compartments and having a anterior convex ramp configured to engage a distal femoral trochlear groove to prevent posterior femoral motion relative to a tibia or anterior tibial translation at full extension of the knee.

In another embodiment, a femoral component of a knee joint prosthesis is provided and can include a lateral femoral condyle having an inferior articulation surface that includes a plurality of convex circular arcs and a concave groove disposed between adjacent convex circular arcs at a posterior portion thereof. The concave groove can be configured for engagement with a convex central region of a lateral tibial surface.

In one embodiment, a femoral component of a knee joint prosthesis is provided and can include a medial femoral condyle having an inferior articulating surface that includes a plurality of convex circular arcs and a concave groove disposed between adjacent circular arcs at a posterior portion thereof configured for engagement with a convex central region of a medial tibial surface.

In another embodiment, a femoral component of a knee joint prosthesis is provided and a lateral femoral condyle having an inferior articulation surface that includes six arcs, and a concave groove disposed between two of the arcs and can be configured for engagement with a convex central-posterior region of a lateral tibial surface. The lateral femoral condyle can further have a contoured superoposterior lateral edge configured to allow for unimpeded rotation of the femur about an overall medial located rotation axis.

In other aspects, a femoral component of a knee joint prosthesis is provided and can include medial and lateral femoral condyles, each having extended superoposterior surfaces configured to allow for stable and low contact stress articulation with a tibial surface in deep flexion.

In further aspects, a femoral component of a knee joint prosthesis is provided and can include a trochlear groove having three regions in the frontal plane. The three regions can include a distal region with a neutral orientation in the medial and lateral dimension, a central portion with a medial orientation, and a proximal region with a neutral to lateral orientation.

In a further embodiment, a femoral component of a knee joint prosthesis is provided and can include a trochlear groove having three regions in the transverse plane. The three regions can include a distal region with a medial tilt in a distal to proximal direction, a central region with a medial tilt greater than the medial tilt of the distal region, and a proximal region with a neutral to medial tilt.

In one embodiment, a knee joint prosthesis is provided and can include a tibial component having an asymmetric tibial post with a curved anterolateral surface and a posterior surface that is rotated laterally. The tibial post can be configured for mating with a femoral component.

In another embodiment, a knee joint prosthesis is provided and can include a tibial component having a base member and separate medial and lateral tibial bearing surfaces mountable upon the base member. The base member can have an anterior bridge connecting the medial and lateral sides thereof that is configured to allow for medial-lateral load sharing to avoid subsidence of medial/lateral tibial surface due to overloading of one side. The anterior bridge can have a groove configured to receive a patellar tendon in deep-flexion and can have a thickness greater than a thickness of the medial and lateral tibial bearing surfaces configured for increased strength.

In one embodiment, a knee joint prosthesis is provided and can include a tibial component having medial and lateral tibial compartments configured to serve as bearing surfaces that articulate with femoral condyles. A posterior portion of the medial and lateral tibial compartments can be positioned distally lower than an anterior portion of the medial and lateral tibial compartments. The distally lower posterior portion can be configured to prevent tibiofemoral joint space overstuffing.

In another aspect, a knee joint prosthesis is provided and can include a femoral component having medial and lateral condyles. The medial condyle can be positioned more distally than the lateral condyle. The knee joint prosthesis can further include a tibial component having medial and lateral compartments configured to serve as bearing surfaces that articulate with the medial and lateral condyles. The medial compartment can be positioned more distally than the lateral compartment, and the femoral and tibial components can be configured to restore the anatomic joint line when mounted on a femur.

BRIEF DESCRIPTION OF THE DRAWINGS

The invention will be more fully understood from the following detailed description taken in conjunction with the accompanying drawings, in which.

DETAILED DESCRIPTION OF THE INVENTION

Various embodiments of the invention provide improved knee prostheses for replacing at least a portion of a knee joint between the distal end of a femur and the proximal end of a tibia.

Embodiments of the invention provide knee prostheses which more faithfully and closely replicate the function, anatomy and physiology of the normal human knee yielding a number of advantages. Among other things, such prostheses can provide an increased range of motion and function more normally particularly in extension, deep flexion and during normal gait. Knee prostheses according to various aspects of the invention recognize that during movement of the knee, particularly during flexion, the kinematics of the bones of the knee are a result of achieving equilibrium of the forces that cause motion of the knee. In addition, the shape of the articular surfaces acting in combination with forces imposed by various muscles, ligaments and tendons, determines the direction of the large contact forces.

Conventional knee prostheses have been developed without accounting for the full range of kinetics of active knee movement. Many are primarily concerned with achieving greater flexion. However, in addition to flexion and extension, motion of the knee is both rotational and translational. The femoral condyles both roll and glide as they articulate with respect to the tibial plateaus. As the knee moves from full extension into flexion the axis of rotation between the femur and the tibia moves posteriorly relative to both the femur and the tibia. Additionally, in the normal human knee, internal rotation of the tibia relative to the femur occurs as the knee flexes between full extension and approximately 150 degrees of flexion. Knee prostheses according to various embodiments of the invention provide various surfaces on at least the femoral component and the tibial component which promote greater flexion, internal rotation of the tibia relative to the femur as the knee flexes, and other characteristics of the natural knee.

Figure 1A:
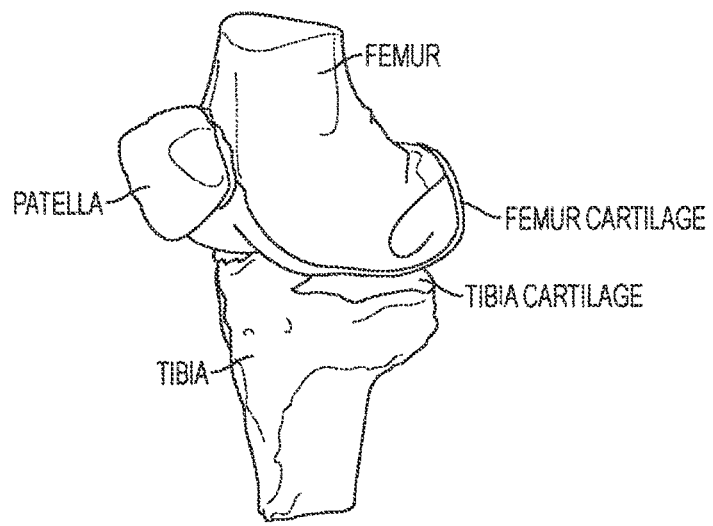
FIG. 1A is a perspective view of a normal human knee.
Figure 1B:
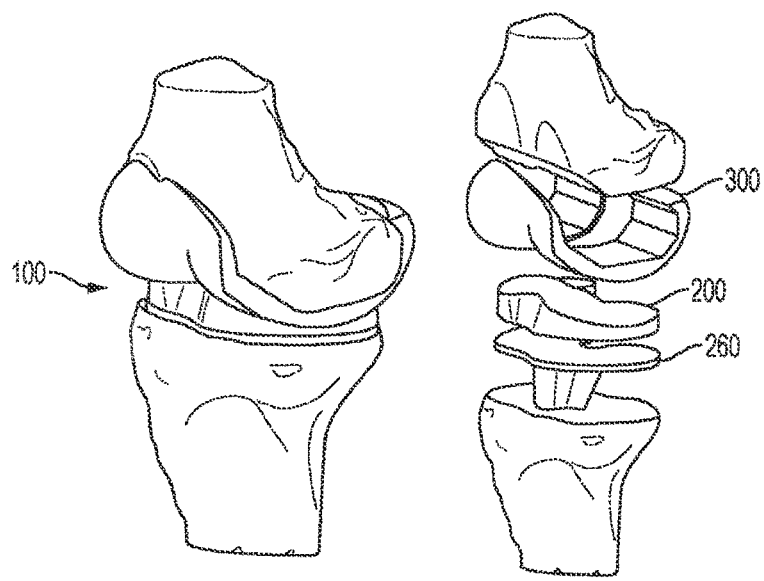
FIG. 1B is a perspective view of an exemplary knee prosthesis.
Figure 1C:
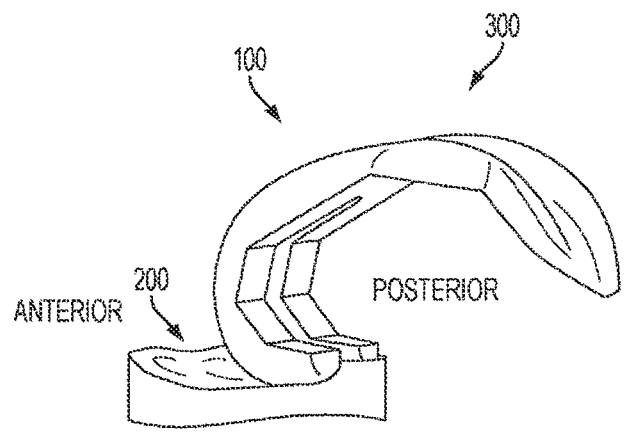
FIG. 1C is a perspective view of one embodiment of a femoral component and a tibial component of the knee prosthesis of FIG. 1B.
Figure 1D:
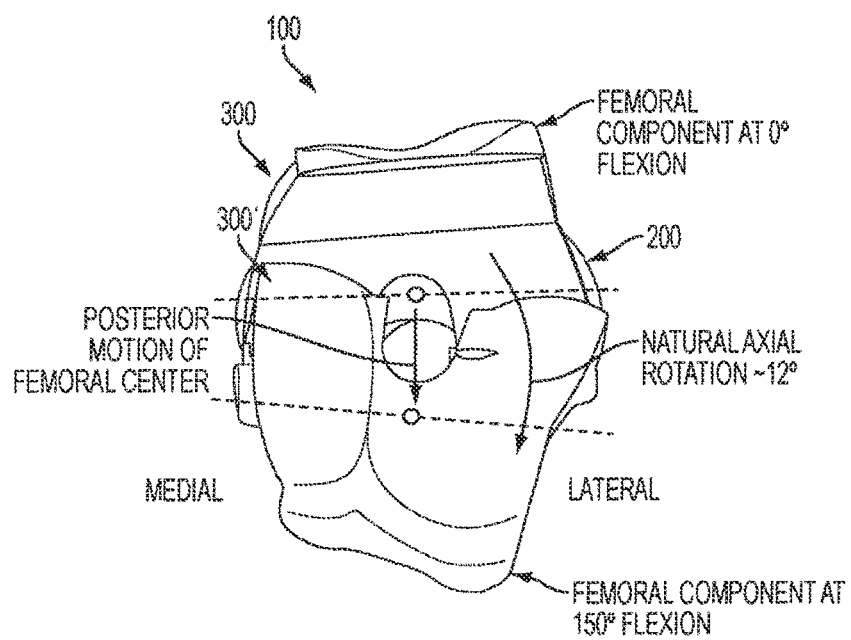
FIG. 1D is a top perspective view of the femoral component of FIG. 1C in 0 degrees flexion and 150 degrees flexion.

A typical knee joint without a knee prosthesis is illustrated in FIG. 1A. The femur and tibia are shown with healthy femur and tibia cartilage. An exemplary embodiment of a portion of a knee prosthesis according to the invention is shown in FIGS. 1B-1D. A knee prosthesis 100 is provided and is designed to replace at least a portion of a knee joint (the right knee is shown) between the distal end of a femur and the proximal end of a tibia. A mirror image (not shown) of knee prosthesis 100 will replace at least a portion of a left knee between the distal end of a femur and the proximal end of a tibia. As shown, the knee prosthesis 100 can include a tibial component 200 for mounting to a proximal end of a resected tibia, or to another prosthesis element such as a tibia base 260 that is mated to a resected tibia, and a femoral component 300 for mounting to a distal end of a resected femur.

FIG. 1D illustrates the femoral component 300 at 0 degrees flexion and a femoral component 300' at 150 degrees flexion. As shown, as the femoral component 300 moves between these two flexion points, the femur experiences axial rotation about an overall medially located pivot point and posterior motion of the its center. In some embodiments, the femoral component can rotate with an axial rotation of about 12 degrees. In other embodiments, the axis of rotation can be in the ranges of 1 degree to 30 degrees, 5 degrees to 25 degrees, 8 degrees to 20 degrees, 10 degrees to 15 degrees, etc. In addition, in its movement between 0 degrees flexion and 150 degrees flexion, a center axis of the femoral component 300 can translate posteriorly as indicated by FIG. 1C and by the center arrow in FIG. 1D. While the distance that the femoral center will translate during flexion can vary depending on the size of the implant, in one embodiment, the femoral center can translate about 28 mm. In other embodiments, the femoral center can translate in the ranges of 12 mm to 45 mm, 15 mm to 40 mm, 18 mm to 40 mm, 20 mm to 38 mm, 24 mm to 33 mm, 26 mm to 30 mm, etc.

Figure 2:
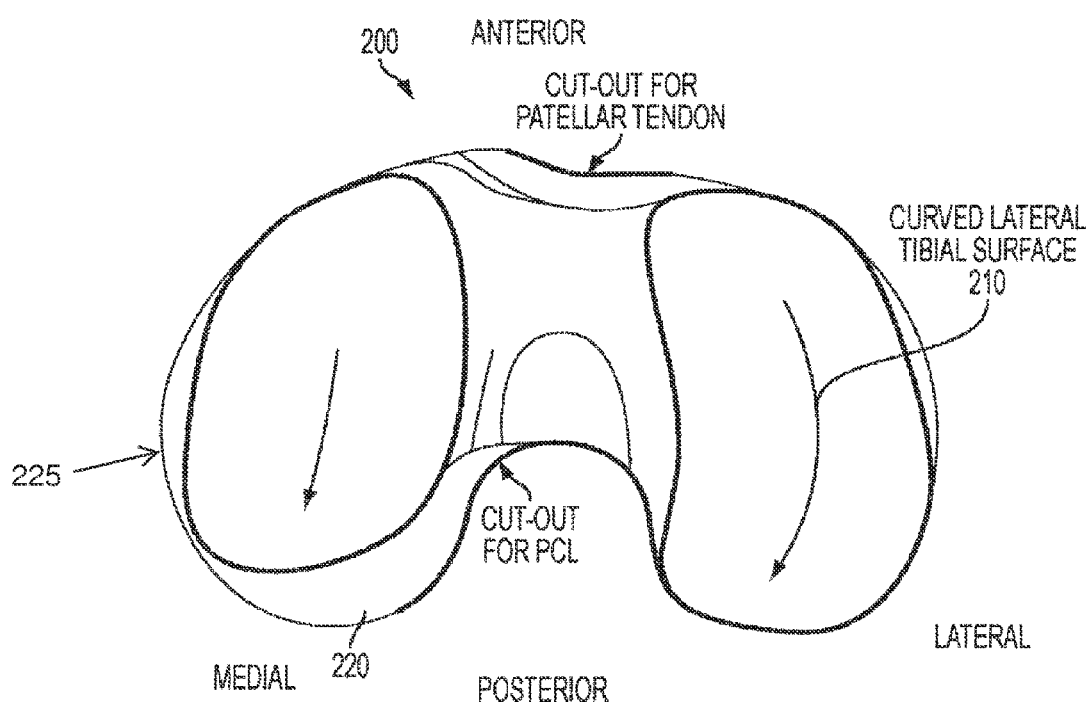
FIG. 2 is a top view of the tibial component of FIG. 1C.

The tibial component 200 is shown in more detail in FIG. 2. The tibial component 200 can be constructed in various manners and out of various materials. The tibial component 200 can be machined, cast, forged or otherwise constructed as a one-piece integral unit, or a two-piece unit, out of a medical grade, physiologically acceptable material such as polyethylene (e.g., high molecular weight polyethylene and/or vitamin E containing high molecular weight polyethylene) or the like, in various sizes to fit a range of typical patients, or it can be custom designed for a specific patient based on data provided by a surgeon after physical and radiography examination of the specific patient. As noted above, the tibial component 200 can be configured for use with a tibial base 260. In other embodiments, the tibial component 200 can be used without a tibial base 260, with appropriate modifications known to those skilled in the art, and can be implanted directly on a resected tibia.

In some embodiments, the tibial component 200 can have asymmetric medial and lateral compartments 220, 210, which interact with asymmetric medial and lateral condyles of the femoral component 300 (described below) to restore normal/physiologic knee motion characterized by: (a) axial rotation of the femur about an overall medially located pivot point, and (b) posterior motion of the femur center, with knee flexion, as illustrated in FIGS. 1C and 1D. This motion of the femur relative to the tibia can also be described as overall greater posterior motion of the lateral femoral condyle relative to the medial femoral condyle as the knee bends from 0° to 150° flexion (FIG. 1D). In some embodiments for partial knee replacement, a compartment 220, 210 can be used alone and/or in combination with a center portion (described below) and/or in combination with the tibial base 260. An overall size of the tibial component 200 can vary depending on the size of the patient. In some embodiments, a lateral width of the tibial component 200 from a lateral wall of the lateral component 210 to a medial wall of the medial component 220 can be about 74 mm. In other embodiments, the overall width can be in the range of 45 mm to 95 mm, 50 mm to 90 mm, 55 mm to 95 mm, 60 mm to 80 mm, 65 mm to 75 mm, etc.

Figure 3A:
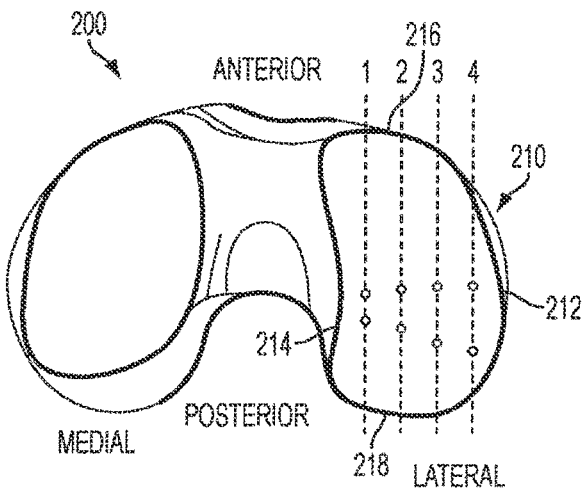
FIG. 3A is a top view of the tibial component of FIG. 1C illustrating the curvature of a lateral tibial compartment.
Figure 3B:
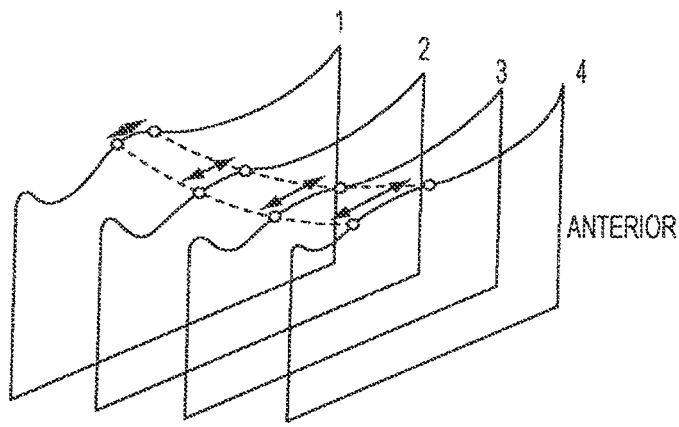
FIG. 3B is an illustration of the curvature of the lateral tibial compartment of FIG. 3A.
Figure 3C:
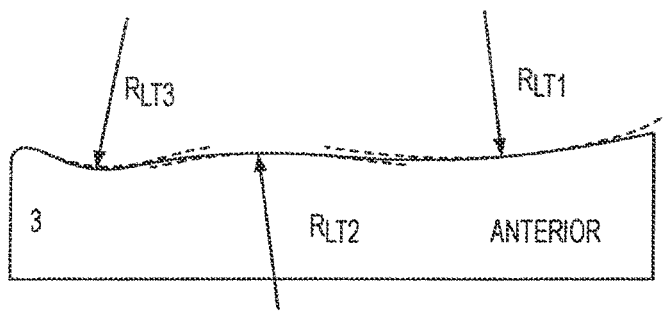
FIG. 3C is an illustration of the curvature of the lateral tibial compartment of FIG. 3A.

The lateral tibial compartment 210, shown in more detail in FIGS. 3A-3C, can have a shape, such as a kidney bean shape, that curves about a medially located center 223 (see FIG. 2). The lateral tibial compartment 210 can be defined by a lateral sidewall 212 with a concave curvature relative to the compartment 210 and can have a medial sidewall 214 with a convex curvature relative to the compartment 210. A length of the lateral sidewall 212 can be longer than a length of the medial sidewall 214 such that the lateral tibial compartment 210 curves about a medial point forming the kidney bean shape. The lateral tibial compartment 210 can also be defined by an anterior endwall 216 and a posterior endwall 218 with an elongated length of the lateral tibial compartment 210 extending therebetween. The endwalls 216, 218 can both have a concave curvature relative to the lateral tibial compartment 210 that joins with the curvature of the lateral and medial sidewalls 212, 214. In some embodiments, a length between the endwalls 216, 218 can be about 50 mm, although this dimension will change depending on the size of the patient. For example, the length between the endwalls 216, 218 can also be in the range of 30 mm to 70 mm, 35 mm to 65 mm, 40 mm to 60 mm, 45 mm to 55 mm, etc.

Figure 4:
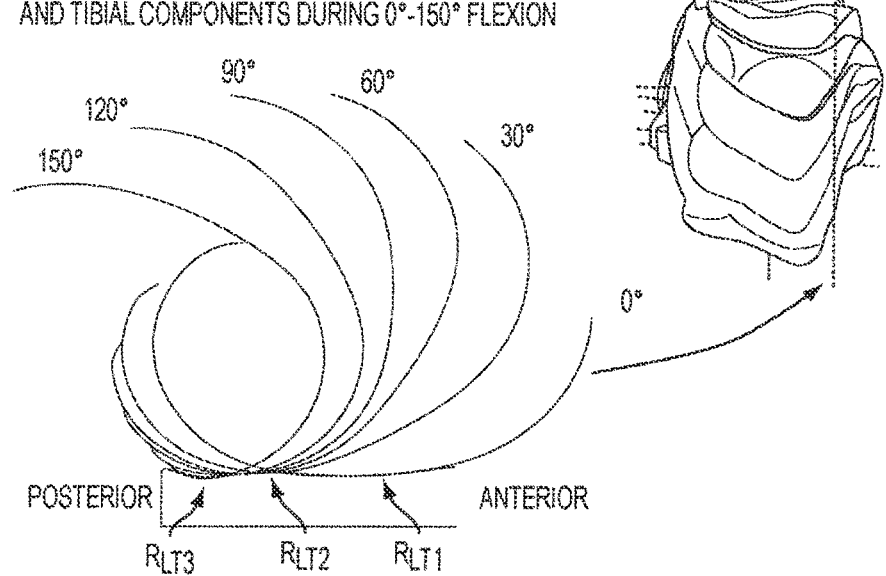
FIG. 4 is an illustration of the femoral component of FIG. 1C moving over the lateral tibial compartment of FIG. 3A.

The lateral tibial compartment is generally concave in both the coronal and sagittal planes. In the anterior-posterior direction, the lateral tibial compartment 210 can have, for example, three distinct regions that function during different phases of knee flexion. The first region $R_{LT1}$, illustrated most clearly in FIG. 3C, is an anteriorly located surface that can have a concave or dished geometry. The first region $R_{LT1}$ can be functional in early flexion, for example, in the range of about 0 degrees to about 30 degrees flexion and can have a radius of curvature of, for example, about 70 mm. As will be appreciated by those skilled in the art, the first region $R_{LT1}$ can have any radius of curvature as needed, for example in the range of 50 mm to 90 mm, 55 mm to 85 mm, 60 mm to 80 mm, 65 mm to 75 mm, etc. A mediolateral width of the first region $R_{LT1}$ can be about 22 mm, although it can have any width as needed, for example, in the range of 12 mm to 30 mm, 15 mm to 28 mm, 20 mm to 25 mm, etc. FIG. 4 illustrates the femoral component 300 as it progresses through its full range of flexion over the lateral tibial compartment 210. The anterior first region $R_{LT1}$ can cover approximately 50% of the lateral compartment 210, although it can cover any percentage of the compartment as needed. As illustrated in FIG. 4, the femoral component 300 is in contact with region $R_{LT1}$ from about 0 degrees to about 30 degrees.

A second, central region $R_{LT2}$ can have a dome-shape or convex curvature, as shown in FIG. 3C. The anteroposterior extent of this central region $R_{LT2}$ can be shortest near the inner edge of the lateral tibial compartment 210 and greatest towards the outer edge. For example, the medial most anteroposterior width of the central region $R_{LT2}$ can be about 6 mm while the lateral most anteroposterior width of central region $R_{LT2}$ can be about 11 mm, although both widths can be any size as needed for a particular sized patient, for example, both widths can be in the range of 1 mm to 20 mm, 3 mm to 18 mm, 4 mm to 15 mm, etc. This is shown most clearly in FIGS. 3A and 3B. FIG. 3B illustrates the contours of the lateral tibial compartment 210. The anteriorly positioned line of dots in FIG. 3A represents the transition from the anterior first region $R_{LT1}$ to the central region $R_{LT2}$. The posteriorly positioned line of dots represents the transition from the central region $R_{LT2}$ to the posterior third region Rum, described below. As shown, the central region $R_{LT2}$, defined by the two lines of dots, expands in width moving laterally across the lateral tibial compartment 210. This "fanning" of the central region $R_{LT2}$ can allow for the femoral component 300 to rotate about an overall medially located axis. The central region $R_{LT2}$ can be functional during mid-range of knee flexion, for example, in the range of about 30 degrees and about 75 degrees flexion, as shown in FIG. 4, and can have a radius of curvature of about 36 mm, although the radius of curvature can also be in the range of 20 mm to 50 mm, 25 mm to 45 mm, 30 mm to 40 mm, etc. A mediolateral width of the region $R_{LT2}$ can be about 24 mm, although it can have any width as needed, for example, in the range of 12 mm to 30 mm, 15 mm to 28 mm, 20 mm to 25 mm, etc. The central region $R_{LT2}$ can mark the transition of the lateral femoral condyle to the third and most posterior region $R_{LT3}$ of the lateral tibial compartment 210.

The posterior third region $R_{LT3}$ can be functional during mid-to-deep knee flexion, for example, in the range of about 75 degrees to about 150 degrees flexion, as shown in FIG. 4, and can have a radius of curvature of about 12 mm, although the radius of curvature can also be in the range of 1 mm to 25 mm, 3 mm to 20 mm, 5 mm to 18 mm, etc. A mediolateral width of the first region $R_{LT1}$ can be about 22 mm, although it can have any width as needed, for example, in the range of 12 mm to 30 mm, 15 mm to 28 mm, 20 mm to 25 mm, etc. The convex or dished geometry of the region $R_{LT3}$ can allow for stable and high conformity articulation with the femur even in deep flexion (greater than about 120 degrees). Additionally, the posterior third region $R_{LT3}$ can function with the central convex region $R_{LT2}$ to prevent the lateral femoral condyle from sliding anteriorly, which would lead to loss of physiologic knee rotation and posterior femoral translation, as happens in current knee prostheses. A total length of the three regions of the lateral tibial compartment 210 can be about 46 mm at the cross-section number 3 in FIG. 3A, although the size can vary depending on the size of the patient.

The medial tibial compartment 220 is illustrated in more detail in FIGS. 5A-5D and can be shorter in extent compared to the lateral compartment 210. While the medial compartment 220 can have many configurations, in the illustrated embodiment, the medial compartment 220 is oriented such that it is relatively straight in the anteroposterior direction. The medial tibial compartment 220 can be defined by a relatively straight lateral sidewall 222 and a relatively straight medial sidewall 224, although as will be appreciated by those skilled in the art, the sidewalls 222, 224 can have some curvature, for example, a concave curvature, relative to the medial tibial compartment 220. A length of the lateral sidewall 222 and a length of the medial sidewall 224 can be substantially the same and/or one sidewall 222, 224 can have a length somewhat longer or shorter than the other. The medial tibial compartment 220 can also be defined by an anterior end wall 226 and a posterior end wall 228 with an elongate length of the lateral tibial compartment 220 extending therebetween. The endwalls 226, 228 can both have substantially concave curvatures relative to the medial tibial compartment 220. In some embodiments, a length between the endwalls 226, 228 can be about 42 mm, although this dimension will change depending on a size of the patient. For example, the length between the endwalls 226, 228 can also be in the range of 25 mm to 65 mm, 30 mm to 60 mm, 35 mm to 55 mm, 40 mm to 50 mm, etc. The shorter length of the medial compartment 220 compared with the length of the lateral compartment 210 and the relative straightness of the medial compartment 220 can limit the overall posterior motion of medial femoral condyle compared to the lateral femoral condyle and allow for femoral rotation about a medial pivot. The medial compartment 220 includes a medial edge 225 (see FIG. 2).

The medial tibial compartment 220 is generally concave in both the coronal and sagittal planes. A sagittal plane cross-section of the medial tibial compartment 220 can have two possible geometries. In one embodiment, shown in FIGS. SB and SC, the medial tibial compartment 220 can have a concave or dished geometry with a relatively long, large radius of curvature concave anterior region $R_{MT1}$, and a relatively short, small radius of curvature region $R_{MT2}$ between the anterior-posterior regions. For example, the radius of curvature in the region $R_{MT1}$ can be about 60 mm, while the radius of curvature in the region $R_{MT2}$ can be about 22 mm, although the radius of curvature in the region $R_{MT1}$ can be in the range of 40 mm to 80 mm, 45 mm to 75 mm, 50 mm to 70 mm, 55 mm to 65 mm, etc. Likewise, the radius of curvature in the region $R_{MT2}$ can be in the range of 5 mm to 40 mm, 10 mm to 35 mm, 15 mm to 30 mm, etc. A mediolateral width of the first region $R_{MT1}$ and the second region $R_{MT2}$ can be about 19 mm, although it can have any width as needed, for example, in the range of 12 mm to 30 mm, 15 mm to 28 mm, 18 mm to 23 mm, etc.

Figure 6:
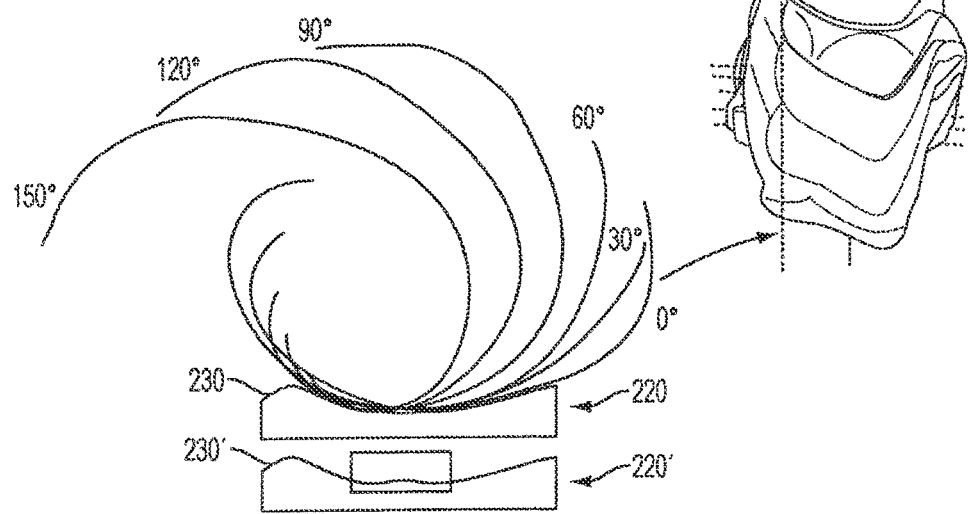
FIG. 6 is an illustration of the femoral component of FIG. 1C moving over the medial tibial compartment of FIG. 5A.

A line of dots shown in FIGS. SA and SB illustrates the transition point between the two regions $R_{MT1}$, $R_{MT2}$. During early/low flexion, for example, flexion less than 30 degrees, the lateral tibiofemoral contact is restricted to the concave anterior region ($R_{LT1}$, FIG. 3C) of the lateral tibial compartment 210, while the medial tibiofemoral contact is less constrained due to the overall concave geometry of the medial tibial compartment 220, as shown in FIG. 6. This allows for femoral rotation about a lateral axis during early/low flexion, characteristic of normal knee motion during walking. However, the overall longer extent of the lateral tibial compartment 210 compared to the medial compartment 220 results in external femoral rotation about a medial axis during mid-to-deep flexion, characteristic of normal knee motion during other activities like squatting that involve deeper knee flexion. A mediolateral width at the transition point can be about 25 mm, although it can have any width as needed, for example, in the range of 12 mm to 30 mm, 15 mm to 28 mm, 20 mm to 26 mm, etc.

Figure 5A:
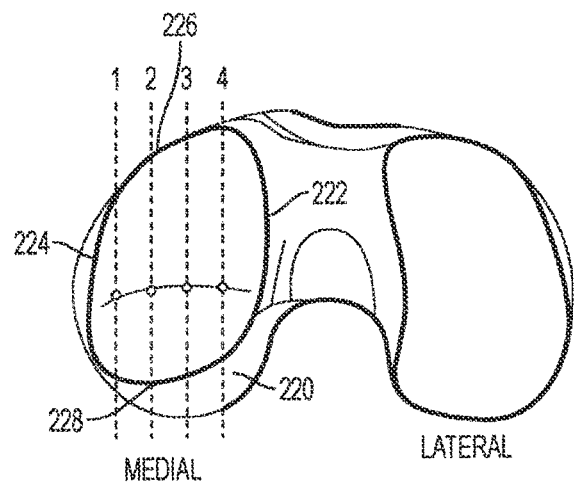
FIG. 5A is a top view of the tibial component of FIG. 1C illustrating the curvature of a medial tibial compartment.
Figure 5B:
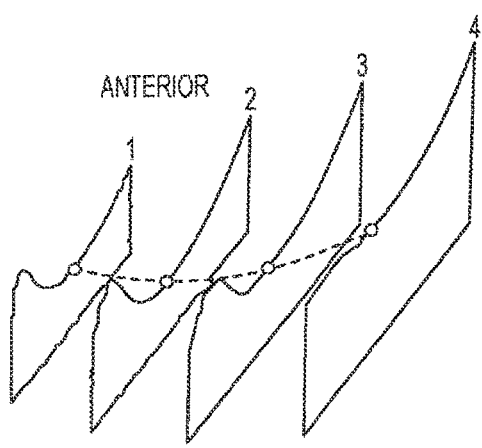
FIG. 5B is an illustration of the curvature of the medial tibial compartment of FIG. 5A.
Figure 5C:
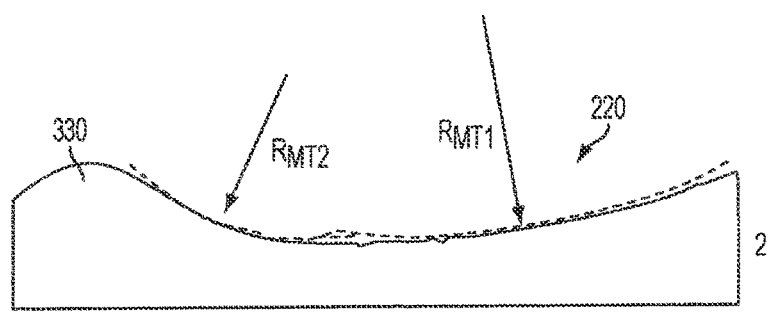
FIG. 5C is an illustration of the curvature of the medial tibial compartment of FIG. 5A.
Figure 5D:
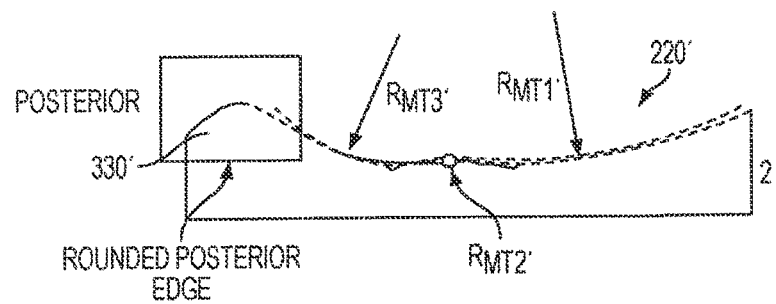
FIG. 5D is an illustration of another embodiment of the curvature of the tibial compartment of FIG. 5A.

Another embodiment of a medial compartment 220' is illustrated in FIG. 5D. In this embodiment, the medial compartment 220' can be composed of three regions similar to the lateral compartment 210, although with some differences. The first and third regions $R_{MT1}$, $R_{MT3}$ can be the same or similar to the first and second regions $R_{MT1}$, $R_{MT2}$ of the medial compartment 220. A central convex dome-shaped region $R_{MT2}$ can be disposed between the first and third regions $R_{MT1}$, $R_{MT3}$ and can be relatively short in extent compared to the anterior and posterior regions $R_{MT1}$, $R_{MT3}$. In addition, the anteroposterior extent of the central region $R_{MT2}$ can change little from an inner edge to an outer edge of the medial compartment 220', i.e. there is no "fanning" as on the lateral compartment 210. The radius of curvature of the central region $R_{MT2}$ can be about 20 mm, although it can also be in the range of 5 mm to 35 mm, 10 mm to 30 mm, 15 mm to 25 mm, etc. The shorter extent of the medial central region $R_{MT2}$ also implies that the transition of the tibiofemoral contact from anterior to posterior region of the tibia happens later and over a relatively shorter range of flexion, for example, in the range of about 60 degrees to about 90 degrees flexion, compared to on the lateral side in the range of about 30 degrees to 75 degrees flexion.

FIG. 6 illustrates the femoral component 300 moving over the medial compartments 220, 220'. Sagittal plane cross-sections passing through the medial side of the femoral and tibial components 200, 300 are illustrated as the knee moves from 0 to 150° flexion. With medial compartment 220, the tibiofemoral contact can be located on the anterior concave region $R_{MT1}$ at low-to-mid flexion, and can transition to the posterior concave region $R_{MT2}$ in mid-to-deep flexion. With medial compartment 220', the tibiofemoral contact can be located on the anterior concave region $R_{MT1}$ at low flexion, and can transition over the central convex region $R_{MT2}$ in mid flexion to the posterior concave region $R_{MT3}$ in deep flexion.

The medial compartment 220, 220' can also have a substantially rounded posterior edge 330, 330' that can prevent early impingement of the medial femoral bone with the medial tibial compartment 220, 220', which would restrict range of knee motion. A radius of curvature of the posterior edge 330, 330' can be about 7 mm, although it can also have a radius in the range of 1 mm to 15 mm, 2 mm to 13 mm, 4 mm to 11 mm, 5 mm to 10 mm, etc. This is one of the factors implicated in the limited range of knee flexion found in contemporary knee prostheses. For more information, see Varadarajan K. M., Moynihan A. L., Seon J. K., Freiberg A., Rubash H. E., Li G., "Changes in Tibiofemoral Joint Space following Total Knee Arthroplasty during Weightbearing Knee Motion," Proceedings of the ASME Summer Bioengineering Conference, Lake Tahoe, Calif., June 2009." The rounded posterior edge 330, 330' can allow for stable contact with the femur bone in deep flexion. In general, the sagittal plane geometry of the medial tibial compartment 220, 220' can be more conforming with the medial femoral condyle than the lateral tibial compartment 210 is with the lateral femoral condyle. Thus the medial side can provide greater stability while the lateral side can provide more mobility. While the regions of the medial compartment 220, 220' can have any length as needed for a particular patient, in one embodiment, an overall length of the regions and the posterior edge 330, 330' can be about 46 mm, although it can also be in the range of 30 mm to 60 mm, 35 mm to 55 mm, 40 mm to 50 mm, etc.

Figure 7A:
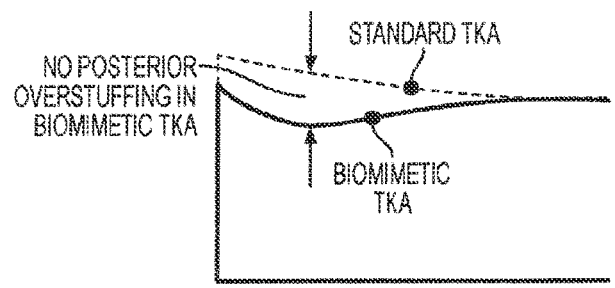
FIG. 7A is an illustration of the lower positioning of the lateral tibial compartment of FIG. 3A compared with traditional knee prostheses.
Figure 7B:
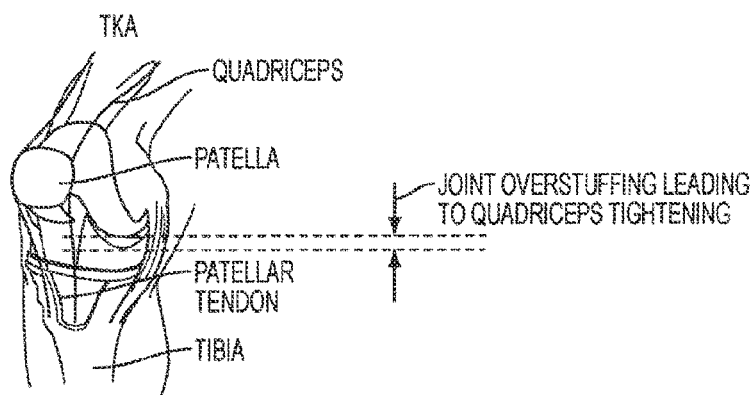
FIG. 7B is an illustration of joint overstuffing in traditional knee prostheses.

In some embodiments, the posterior tibial surfaces of both medial and lateral compartments 210, 220 can be vertically lower than in known prostheses, as shown in FIG. 7A, to avoid posterior tibiofemoral joint space overstuffing seen in knees treated with standard knee prostheses. As used herein, tibiofemoral joint space refers to vertical distance between a fixed point on the femur and a fixed point on the tibia. Positioning the medial and lateral compartments 210, 220 vertically lower than in standard TKA can help to avoid tightening of quadriceps muscle and other soft-tissue structures in deep flexion, thereby enabling increased range of knee flexion, as illustrated in FIG. 7A. For example, as shown in FIG. 7B, a center portion of a superior surface of the lateral tibial compartment 210 can be about 2.5 mm vertically lower than in standard knee prostheses and can be only about 9 mm vertically above a resected tibial surface. As will be appreciated by those skilled in the art, this dimension can vary depending on the size of the patient, and the distance of the superior surface of the lateral tibial compartment 210 can be in the range of 5 mm to 15 mm, 6 mm to 12 mm, etc. above the resected tibial surface.

Figure 8A:
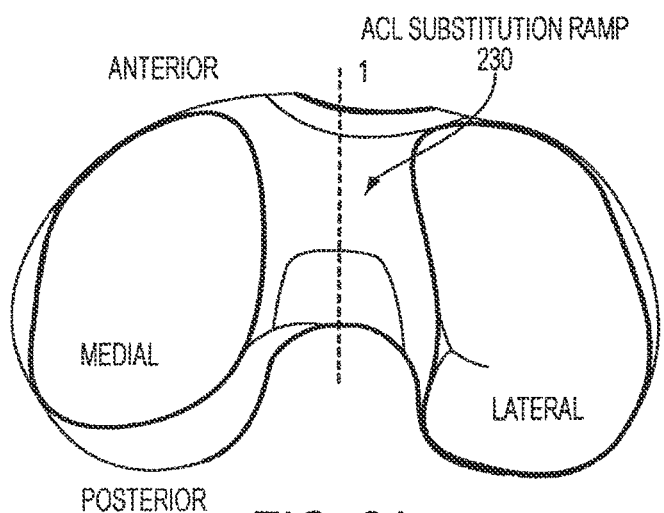
FIG. 8A is a top view of the tibial component of FIG. 1C illustrating the center ramp.
Figure 8B:
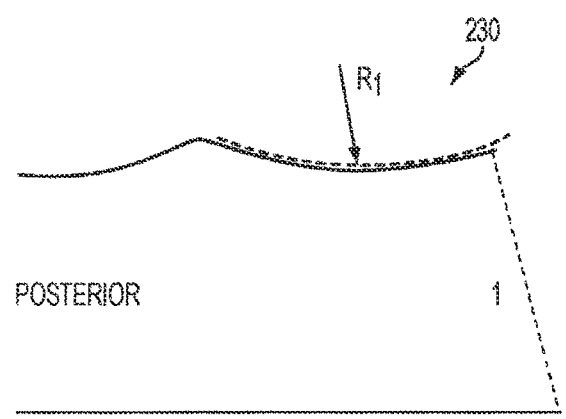
FIG. 8B is an illustration of the curvature of the ramp of FIG. 8A.
Figure 9A:
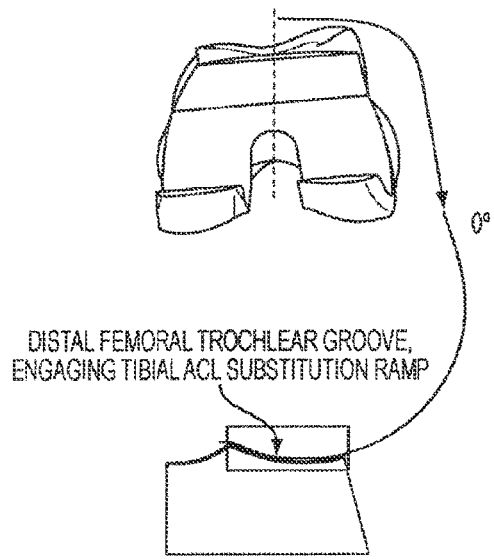
FIG. 9A is an illustration of a trochlear groove of the femoral component of FIG. 1C engaging the ramp of FIG. 8A.
Figure 9B:
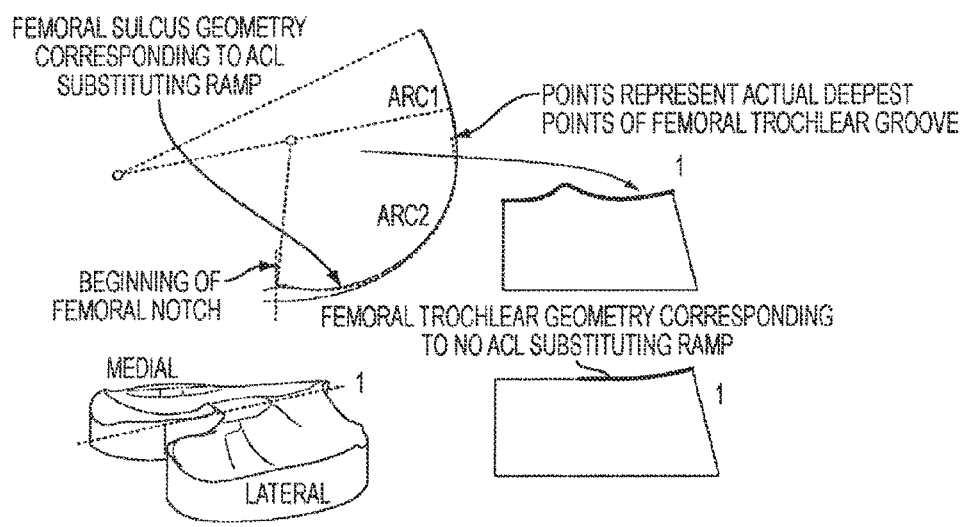
FIG. 9B is an illustration of the curvature of the center portion of the tibial component of FIG. 1C.

In other embodiments, the tibial component 200 of the knee prosthesis 100 can have a central portion disposed between the lateral and medial tibial compartments 210, 220. The center portion can include a concave anterior ramp 230 that acts as a substitute for the anterior cruciate ligament (ACL), as illustrated in FIGS. 8A and 8B. The anterior ramp 230 can be disposed on an anterior side of the center portion and can have a radius of curvature of about 22 mm, although the radius of curvature can be in the range of 12 mm to 30 mm, 15 mm to 25 mm, etc. Often times during TKA procedures, the ACL is cut to facilitate implantation of the prosthesis. As a consequence of the resected ACL, after TKA the femur can have an abnormal posterior location relative to the tibia at full extension (0° flexion). This can be prevented and proper alignment achieved by providing the anterior ramp 230 that can have a concave or dished curvature region $R_{CT1}$ in the sagittal plane. The ramp 230 can engage with the distal femoral trochlear groove, as will be explained in more detail below, to prevent premature/abnormal posterior shift of the femur relative to the tibia, as illustrated in FIGS. 9A and 9B. The femoral trochlear groove can be composed of two arcs, for example arc 1 and arc 2 illustrated in FIG. 9B, that engage with the ramp 230, and which will also be described in more detail below.

Figure 7C:
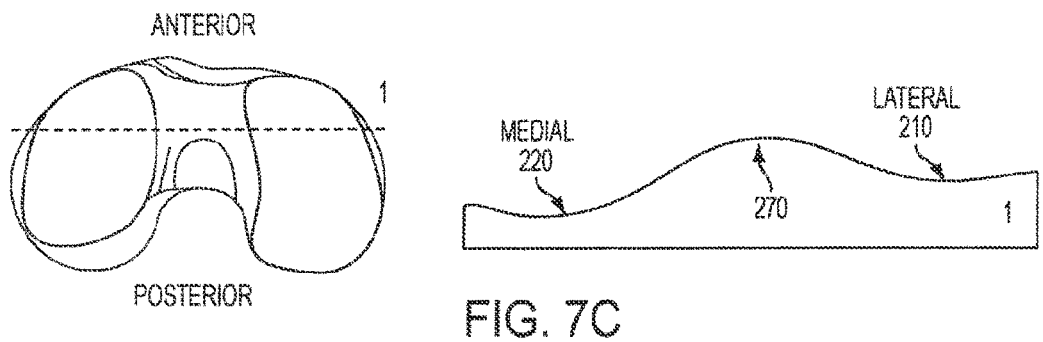
FIG. 7C is a top and rear view of the tibial component of FIG. 1C.

FIG. 7C illustrates a top view of the tibial component and the tibial component 200 from a rear view showing the curvature of the component 200 in the medial/lateral direction. As illustrated, a superior bearing surface of the medial tibial compartment 220 can be vertically lower than a superior bearing surface of the lateral tibial compartment 210. The medial tibial compartment 220 can be concave in the coronal plane and can have a radius of curvature of about 27 mm while the lateral tibial compartment 210 can also be concave in the coronal plane with a radius of curvature of about 24 mm. A center portion 270 of the tibial component 200 can be convex and can have a superior surface vertically higher than the superior surfaces of the medial and lateral tibial compartments 210, 220. The center portion 270 can have a radius of curvature of about 18 mm. Any of these radii of curvature can vary depending on the size of the patient in which the tibial component 200 is to be used. For example, any of the radii of curvature can be in the range of 10 mm to 40 mm, 12 mm to 36 mm, 14 mm, to 32 mm, 16 mm to 28 mm, etc.

Figure 10A:
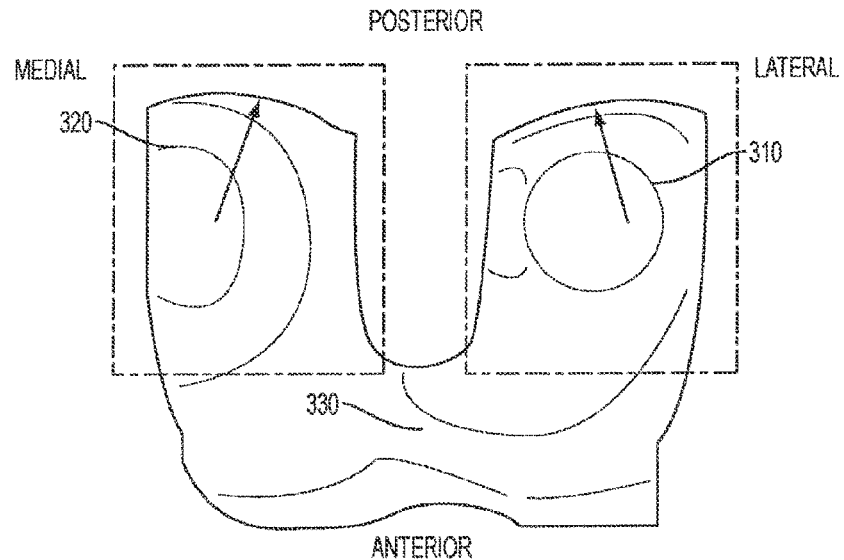
FIG. 10A a top view of the femoral component of FIG. 1C.
Figure 10B:
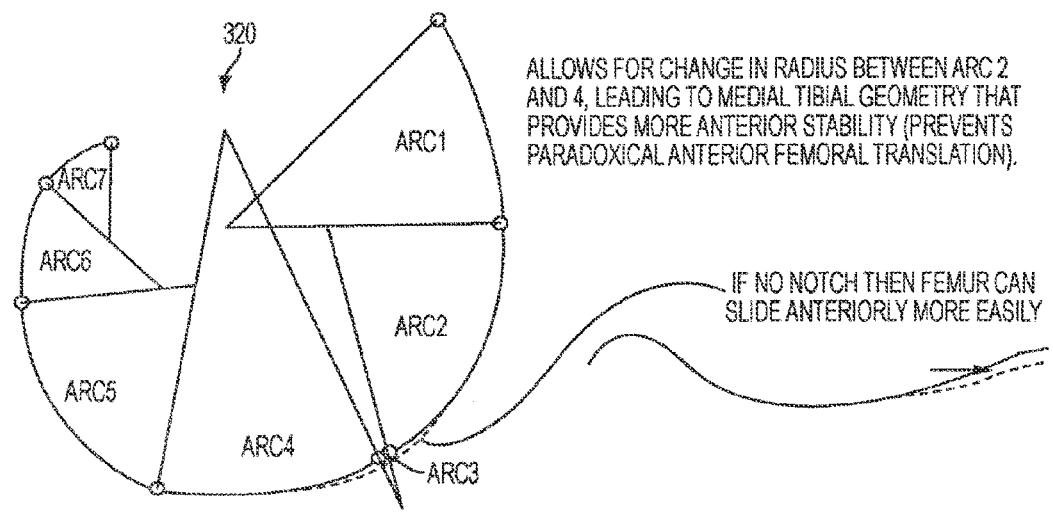
FIG. 10B is an illustration of seven arcs that form one embodiment of a medial femoral condyle.
Figure 10C:
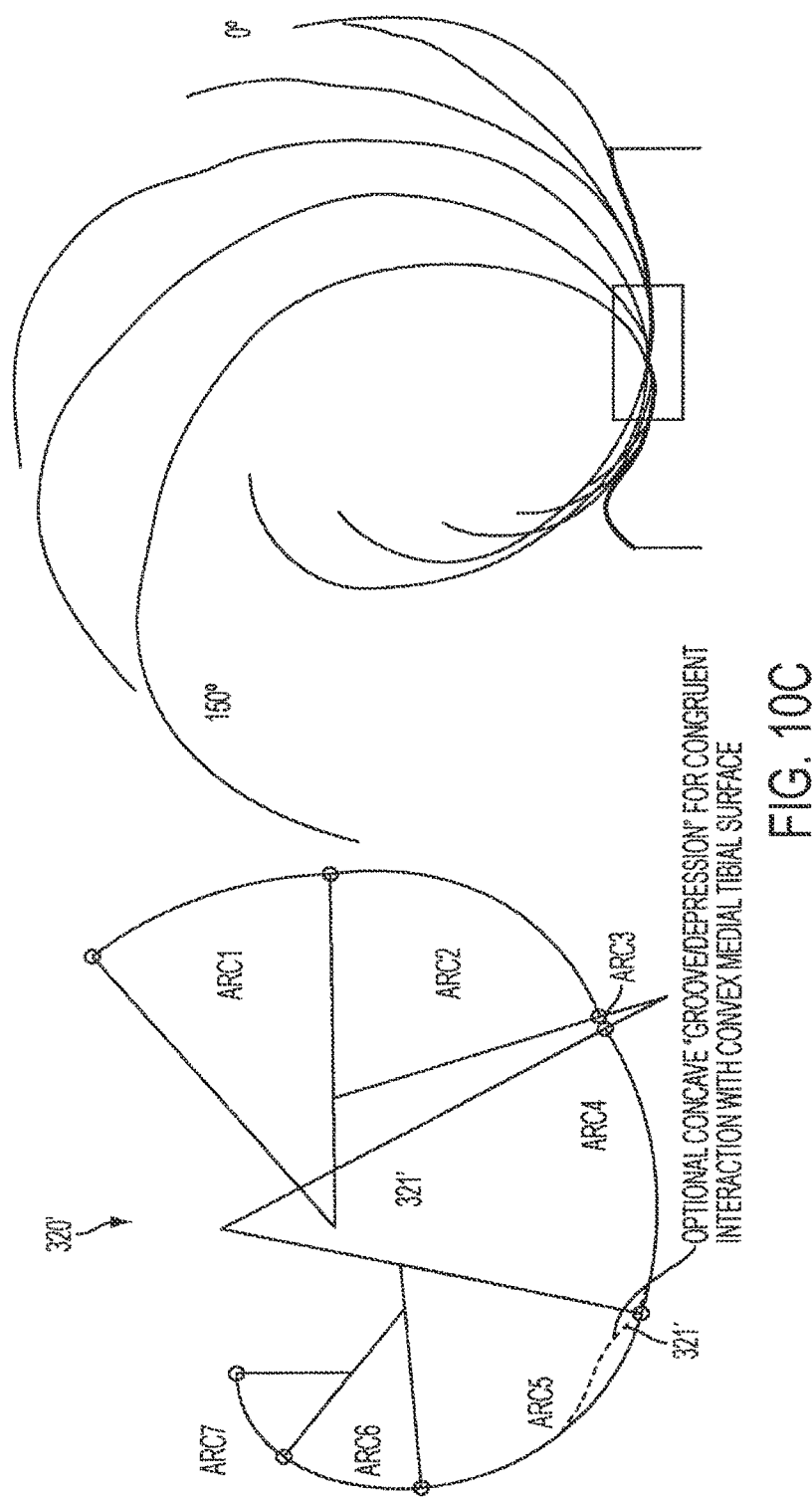
FIG. 10C is an illustration of seven arcs that form another embodiment of a medial femoral condyle.
Figure 11:
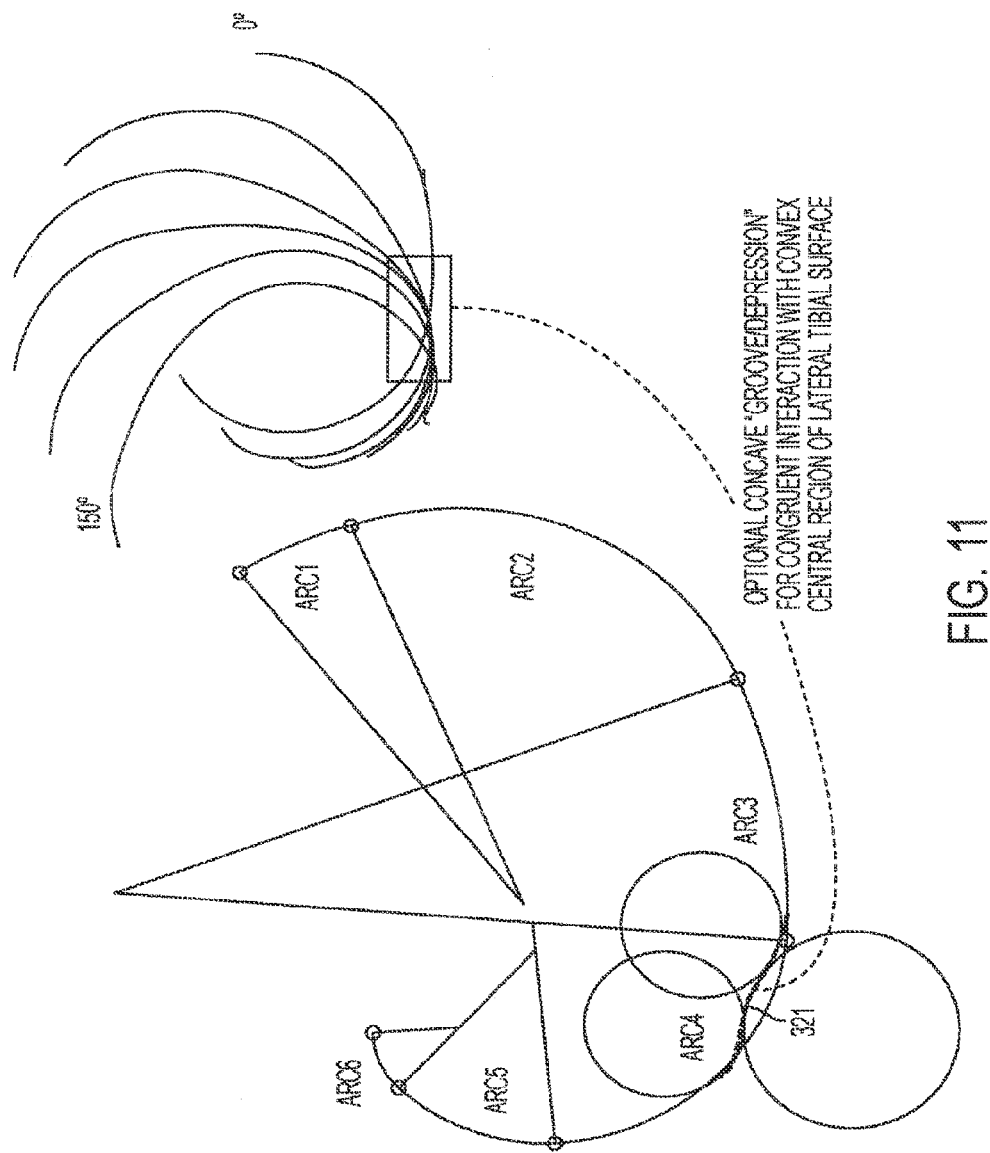
FIG. 11 is an illustration of six arcs that form one embodiment of a lateral femora condyle.

Referring now to FIG. 10A-11, the femoral component 300 is illustrated in more detail. The femoral component 300 can be constructed in various manners and out of various materials. For example, the femoral component 300 can be machined, cast, forged or otherwise constructed as a one-piece integral unit out of a medical grade, physiologically acceptable metal such as a cobalt chromium alloy, a titanium alloy, stainless steel, or the like, in various sizes to fit a range of typical patients, or may be custom-designed for a specific patient based on data provided by a surgeon after physical and radiography examination of the specific patient.

While the femoral component 300 can have many configurations, in one embodiment, the femoral component 300 can include asymmetric medial and lateral condyles 320, 310. The medial and lateral condyles 320, 310 can be configured to interact and articulate with the asymmetric medial and lateral tibial compartments 220, 210. Furthermore the femoral component 300 can have a unique trochlear groove 330 that can provide a more normal patellar tracking as compared to contemporary knee prosthesis designs, and which can interact with the optional ACL substituting tibial ramp 230 to prevent premature posterior shift of the femur. As illustrated in FIG. 10A, the lateral femoral condyle can have a mediolateral radius of curvature of about 22 mm and the medial femoral condyle can have a mediolateral radius of curvature of about 25 mm. As will be appreciated by those skilled in the art, the radius of curvature of the lateral and medial femoral condyles can vary depending on the size needed and can be in the range of 12 mm to 35 mm, 15 mm to 30 mm, 20 mm to 27 mm, etc.

In the sagittal plane, the medial femoral condyle 320 can, in general, be composed of seven circular arcs of varying radii. Arcs 1-7, shown in FIGS. 10B and 10C, progress from the anterior side to the posterior side of the femur. As illustrated in FIG. 10B, arcs 4 to 7 have progressively decreasing radii. Unlike conventional knee prostheses, the medial femoral condyle 320 can have a short concave arc (arc 3) between arcs 2 and 4. Arc 3 can have, for example, a radius of curvature of about 5 mm compared with arc 2 with a radius of curvature of about 24 mm and arc 4 with a radius of curvature of about 44 mm. Arc 3 can allow a smaller radius for arc 4, while maintaining continuity with arc 2. In FIG. 10A, the dotted curve indicates the articular geometry between arc 2 and 4 if arc 3 were removed (as in conventional knee prostheses). The smaller radius of arc 4 can allow the anterior medial tibial compartment 220 to have a smaller radius. This in turn provides greater anteroposterior stability to the femur, thus reducing the unexpected (paradoxical) anterior femoral shift in early flexion commonly seen in knees with conventional knee prostheses. Arc 6 can have a radius of curvature of about 20 mm, although it can have any radius in the range of 10 mm to 30 mm, 12 mm to 28 mm, 15 mm to 25 mm, etc. Arc 1 can have a radius of curvature of about 50 mm, although it can have any radius in the range of 30 mm to 70 mm, 35 mm to 65 mm, 40 mm to 60 mm, 45 mm to 55 mm, etc.

In another embodiment, a medial femoral condyle 320' can have an additional concave region or groove 321' that is included between arcs 4 and 5, as illustrated in FIG. 10C. This concave groove 321' can have a radius of curvature of about 33 mm and can be designed to engage and articulate with the central convex region $R_{MT2}$ on the medial tibial compartment 220' (see FIG. 5D), thus providing congruent interaction with the tibial compartment 220' throughout the range of knee flexion and ensuring smooth transition of tibiofemoral contact from the anterior to the posterior tibial compartment. A person skilled in the art will appreciate that the groove 321' can have any radius of curvature as needed to articulate with the central convex region $R_{MT2}$, for example, 20 mm to 50 mm, 25 mm to 45 mm, 30 mm to 40 mm, etc.

In the sagittal plane, the lateral femoral condyle 310 can be composed of 6 convex circular arcs of different radii, with arcs 3 to 6 having progressively reducing radii, as shown in FIG. 11. Additionally, an optional concave groove 321 can be added between arcs 3 and 4. The concave groove 321 can be configured to engage and articulate with the central convex region $R_{LT2}$ on the lateral tibial compartment 210 (shown in FIG. 3C), thus providing congruent interaction with the tibial compartment 210 throughout the range of knee flexion, and ensuring smooth transition of tibiofemoral contact from the anterior to the posterior tibial compartment 210. The groove 321 can have a radius of curvature of about 60 mm, although it can have any radius in the range of 40 mm to 80 mm, 45 mm to 75 mm, 50 mm to 70 mm, 55 mm to 65 mm, etc. Arc 6 can have a radius of curvature of about 20 mm, although it can have any radius in the range of 10 mm to 30 mm, 12 mm to 28 mm, 15 mm to 25 mm, etc. Arc 1 can have a radius of curvature of about 70 mm, although it can have any radius in the range of 50 mm to 90 mm, 55 mm to 85 mm, 60 mm to 80 mm, 65 mm to 75 mm, etc.

Figure 12A:
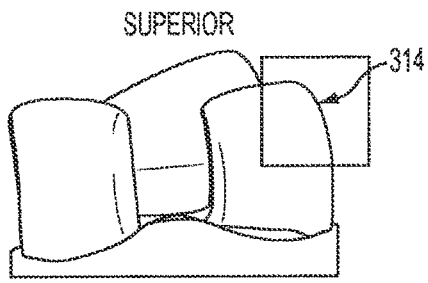
FIG. 12A is a front view of one embodiment of a femoral component illustrating a contoured lateral edge.
Figure 12B:
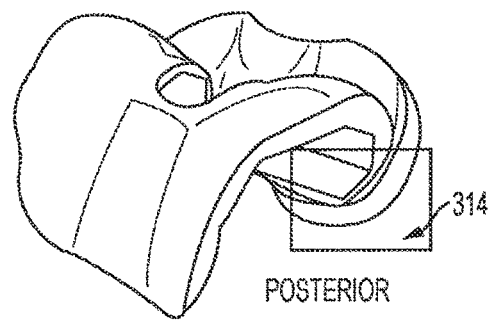
FIG. 12B is a perspective view of the femoral component of FIG. 12A.

In some embodiments, the lateral femoral condyle 310 can have a contoured lateral edge 314 of the superioposterior lateral condyle 310 when viewed from the back, as shown in FIGS. 12A and 12B. This contoured geometry can allow for unimpeded rotation of the lateral femoral condyle 310 about an overall medially located rotation axis.

Figure 13A:
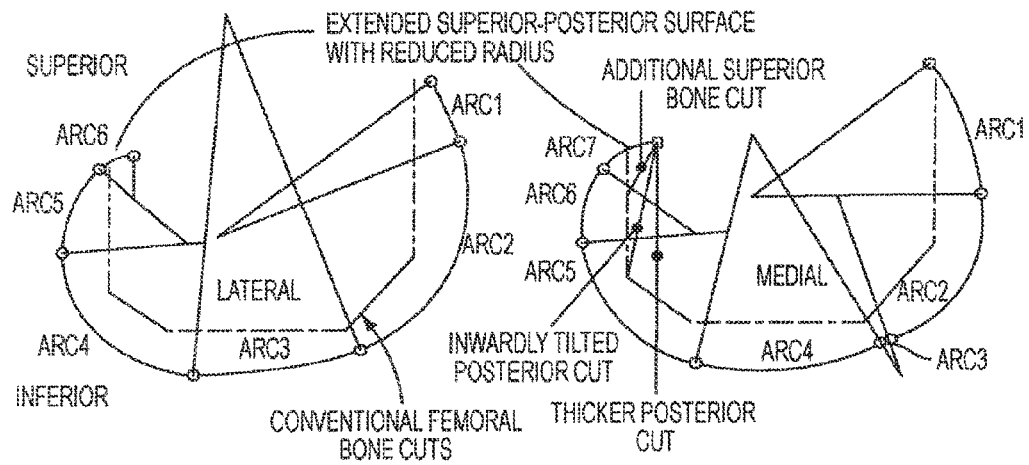
FIG. 13A is an illustration of the arcs of embodiments of the lateral and femoral condyles and the modified femoral bone cuts required to accommodate the femoral condyle geometry.
Figure 13B:
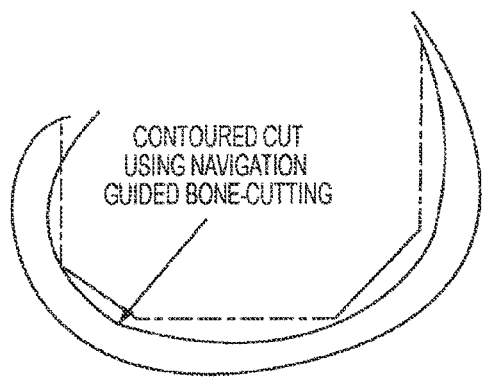
FIG. 13B is an illustration of one embodiment of bone cutting associated with implanting an exemplary femoral component.
Figure 13C:
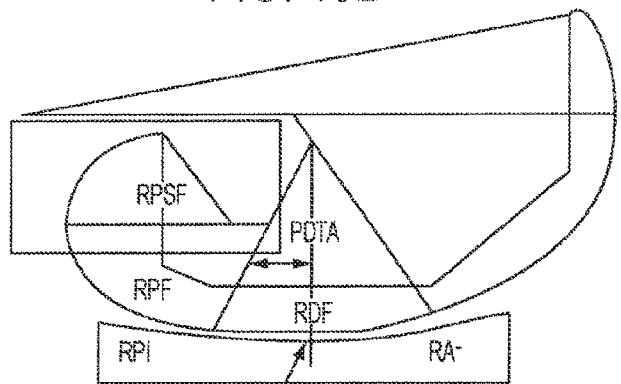
FIG. 13C is an illustration of a prior art femoral component.

Femoral condyles of conventional knee prostheses are typically composed of 5 circular arcs. The medial and lateral femoral condyles 320, 310 end posteriorly near arc 6 on the medial femoral condyle 320 and on arc 5 on the lateral femoral condyle 310, as shown in FIGS. 13A and 13B. Currently known femoral condyles are believed to have only 5 arcs, as illustrated in FIG. 13C. In deep flexion, conventional TKA therefore experiences sharp contact between the femoral and tibial component surfaces. However, the extended superoposterior arcs with reduced radius on the medial and the lateral condyles 320, 310 allow for stable, low stress contact even in very deep flexion (up to 150°). These extended arcs can be accommodated by an additional superoposterior femoral cut, an inwardly angled posterior cut, removing additional bone posteriorly or via a contoured cut using a navigated/robotic cutting tool, as shown in FIGS. 13A and 13B. Arcs 6 on the medial femoral condyle 320 and arc 7 on the lateral femoral condyle can each have a radius of curvature of about 10 mm, although they can have any radius in the range of 1 mm to 20 mm, 5 mm to 15 mm, 8 mm to 12 mm, etc.

Figure 14A:
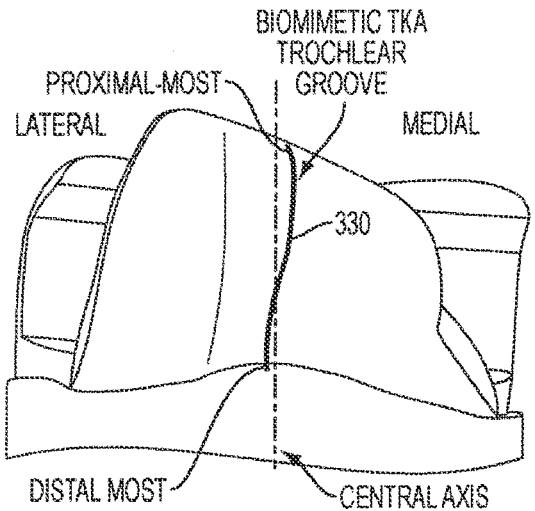
FIG. 14A is a front view of an exemplary trochlear groove.
Figure 14B:
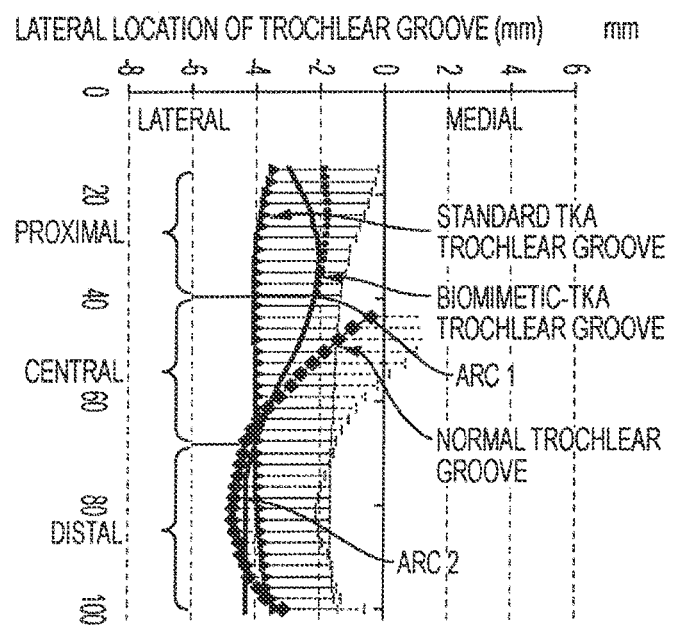
FIG. 14B is an illustration of the lateral location of the trochlear groove of FIG. 14A.

Referring now to FIGS. 14A and 14B, as noted above, in some embodiments, the femoral component 300 can have a femoral trochlear groove 330 for engaging the ACL ramp 230 of the tibial component 200. In the sagittal plane, the femoral trochlear groove 330 can be composed of two circular arcs, with two possible variations in geometry resulting from different radii for the arc 2. In one embodiment, arc 2 can have a relatively small radius corresponding to a more anatomic geometry that leads to an upward sloping lip at the distal end of the trochlear groove, where it meets the distal femoral notch, as illustrated in FIG. 9B. This femoral geometry interacts with the ACL ramp 230 on the tibial component 200 to prevent premature posterior shift of the femur (see FIG. 9A). In another embodiment, arc two can have a larger radius that leads to a downward sloping or horizontal lip at the distal end of the trochlear groove 330. The femoral geometry of this embodiment can function together with a tibial component design that does not have an ACL ramp 230.

When viewed from the front as in FIG. 14A, the femoral trochlear groove 330 can have an orientation that is substantially different from that in conventional knee prostheses, and which can allow for more physiologic patellar tracking. In the normal human knee, the patella glides caudally on the femoral condyles 320, 310 from full extension to full flexion. By 20 to 30 degrees of flexion, the patella first begins to articulate with the trochlear groove. At extreme flexion, the patella lies in the intercondylar recess. Initially, the patella contact occurs distally and with increased flexion the contact areas shift proximally on the patella. Knee prostheses according to certain embodiments and aspects of the invention incorporate features that allow the patellar implant of the knee prostheses to move in a way similar to the normal human knee and to withstand the normal patellofemoral contact force without unnecessary ligament release.

The femoral trochlear groove 330 illustrated in FIGS. 14A and 14B can have three distinct regions. The first and most distal portion, can have a neutral orientation (i.e., not tilted medially or laterally) when viewed from distal to proximal direction, and can be located lateral to the trochlea in standard knee prostheses. The second, central portion can be tilted medially, similar to the natural trochlea, and unlike the neutral orientation in standard knee prostheses. The third and most proximal region can have a neutral oriented trochlea or a laterally oriented trochlea to ensure capture of the patella at full extension (0°).

Figure 15A:
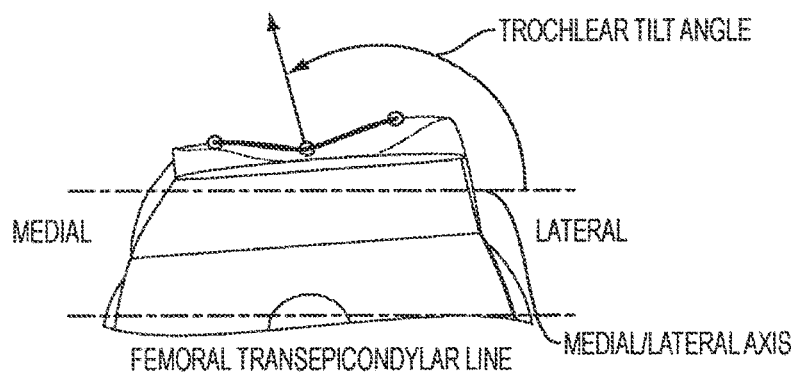
FIG. 15A is a top view of the trochlear groove of FIG. 14A at 0 degrees flexion.
Figure 15B:
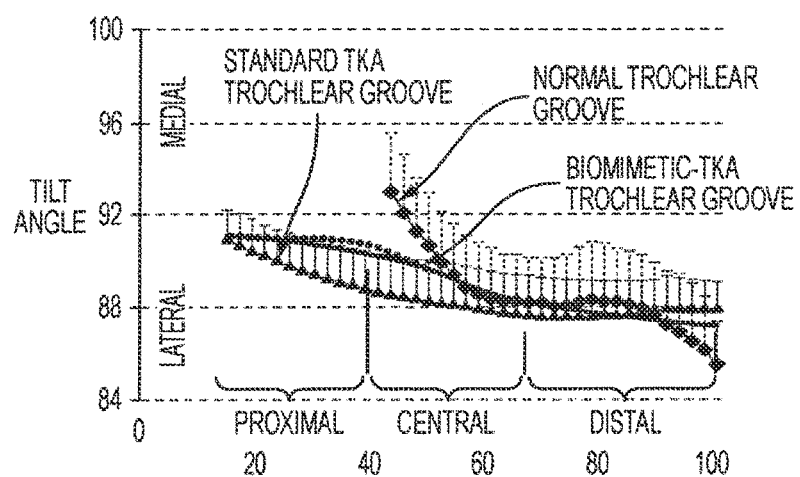
FIG. 15B is an illustration of tilt angle of the trochlear groove of FIG. 14A.

In the transverse plane, illustrated in FIGS. 15A and 15B, the trochlear geometry can also be composed of three regions. The first and most distal portion can have a slight medial tilt (viewed distal to proximal direction), unlike the neutral tilt in the standard TKA. The second, central portion can be tilted more medially, similar to the natural trochlea. The third and most proximal region can have a neutral or slightly medial tilt to ensure capture of the patella at full extension (0° flexion).

Figure 15C:
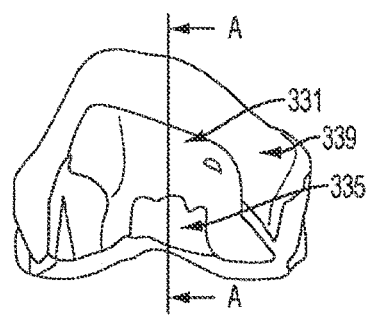
FIG. 15C is an illustration of an exemplary trochlear groove accounting for normal cartilage deformation.
Figure 15D:
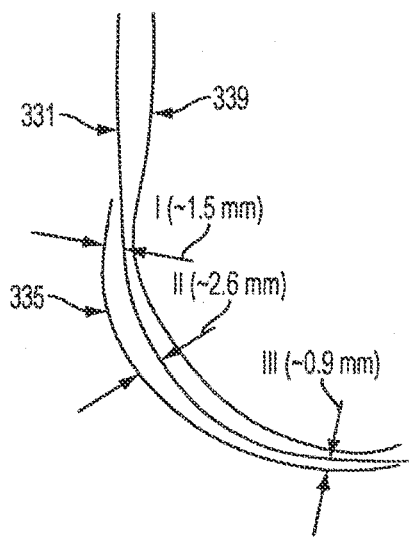
FIG. 15D is a sagittal plane cross-section of the trochlear groove of FIG. 15C.

In some embodiments, an exemplary trochlear groove can be designed to account for the deformation of the femoral and patellar articular cartilage surfaces as the patella moves relative to the femur. Typically the patellar component in TKA is rigid and is mounted to match the height of the native patella. Thus, to account for the cartilage deformation that occurs in the normal knee, an exemplary trochlear groove 331 can be pushed posteriorly and/or proximally toward the body, depending on the region, relative to the femoral trochlear cartilage 335, but can remain anteriorly and/or distally farther from body and from the femoral bone 339. Generally the trochlear groove 331 can be pushed posteriorly and/or proximally, depending in the region, relative to the native articular cartilage 335 by a non-uniform amount along at length of the trochlea 331. In one embodiment, as shown in FIGS. 15C and 15D, the trochlear groove 331 can be pushed posteriorly in the range of about 1 mm to about 2 mm, for example about 1.5 mm, relative to the native cartilage surface 335 in a proximal region I (corresponding to early knee flexion). It can be pushed posteriorly and/or proximally in the range of about 2 mm to about 3 mm, for example about 2.6 mm, relative to the native cartilage surface 335 in a central region II of the trochlea 331 (corresponding to mid-flexion). It can be pushed proximally in the range of about 0.4 mm to about 1.5 mm, for example about 0.9 mm, relative to the native cartilage surface 335 in a distal region III of the trochlea 331 (corresponding to late-flexion). As will be appreciated by those skilled in the art, this concept for designing a femoral trochlear groove surface that accounts for patellofemoral cartilage deformation can also be extended to the design of femoral/tibial articular surfaces to account for tibiofemoral cartilage deformation.

Figure 16A:
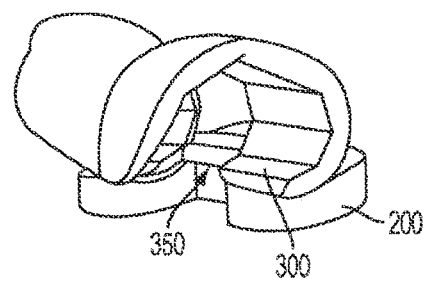
FIG. 16A is a perspective view of one embodiment of knee prosthesis having a cam and post engagement.
Figure 16B:
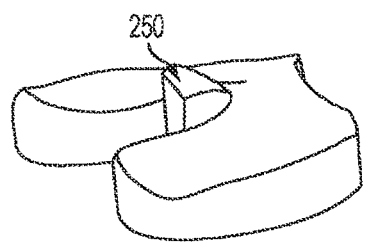
FIG. 16B is a perspective view of the post of FIG. 16A.
Figure 16C:
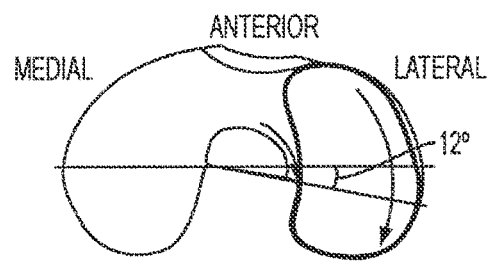
FIG. 16C is a top view of the cam of FIG. 16A.
Figure 16D:
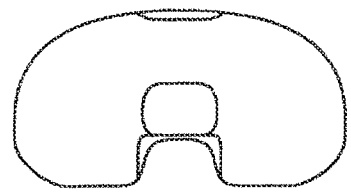
FIG. 16D is a prior art symmetric tibial component.

In some embodiments, the knee prosthesis 100 can include a femoral cam 350 and a tibial post 250, illustrated in FIGS. 16A-16C. The cam 350 and the post 250 can engage at flexion angles above 75 degrees to induce posterior femoral translation, i.e., to substitute the function of the posterior cruciate ligament which is resected in posterior cruciate ligament substituting (PS) TKA procedures. However, unlike standard, symmetric PS prosthesis designs such as that shown in FIG. 16D, a posterior surface of the tibial post 250 can be rotated externally (towards lateral side) to be compatible with the axial rotation of the femur above an overall medially located rotation axis. Additionally, the anterior lateral surface of the tibial post 250 can be curved to be compatible with, and to guide the axial rotation of, the femur.

Figure 17A:
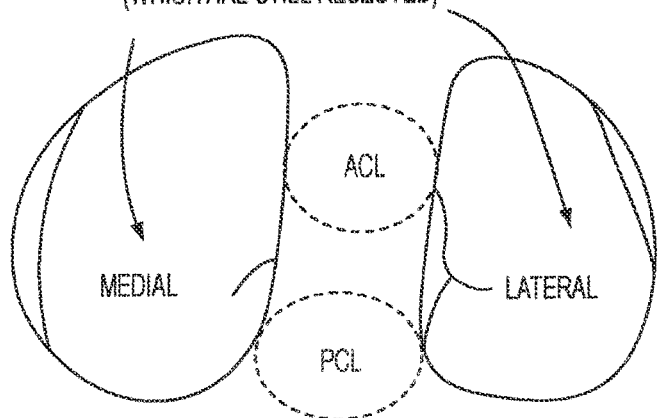
FIG. 17A is top view of another embodiment of a tibial component having separate medial and lateral compartments.
Figure 17B:
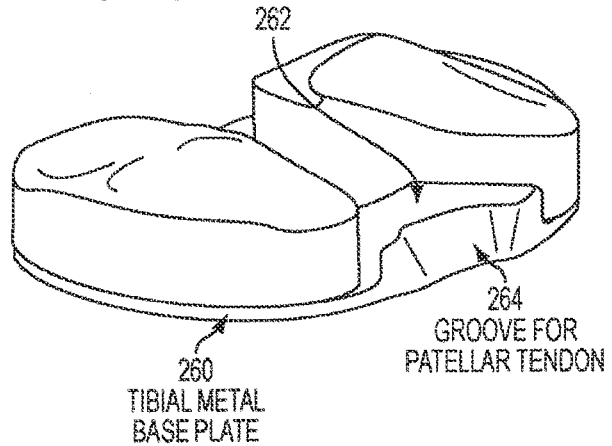
FIG. 17B is a perspective view of the tibial component of FIG. 17A.
Figure 18A:
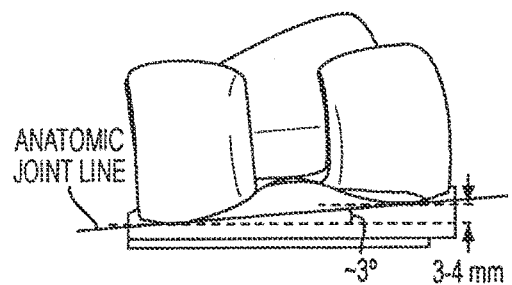
FIG. 18A is a rear view of one embodiment of a knee prosthesis showing the angular difference between the medial and lateral compartments/sides.
Figure 18B:
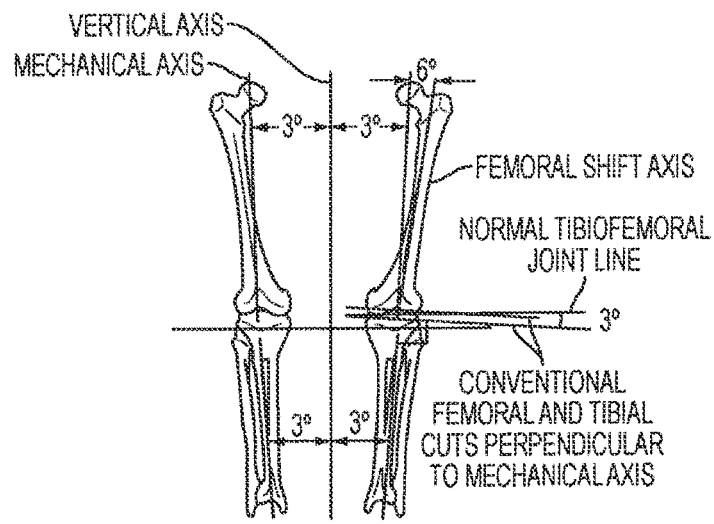
FIG. 18B is an illustration of a knee joint line.

In some TKA procedures, both the anterior and posterior cruciate ligaments can be retained. One embodiment of the knee prosthesis 100, the femoral component 300 and the medial and lateral tibial compartments 220, 210 as described above. However, a cut out for the PCL between the medial and lateral tibial compartments 220, 210 can be extended anteriorly to also allow the ACL to pass between the medial and lateral tibial compartments 220, 210, as illustrated in FIGS. 17A and 17B. The ACL substitution ramp 230 is not required, hence the medial and lateral tibial compartments 220, 210 can be separated. However, the medial and lateral sides can still share load through, for example, a one piece tibial metal base plate 260, which can have an anterior bridge 262 connecting the medial and lateral sides. The base plate 260 can have any suitable thickness as needed, but one embodiment, it has a thickness of about 2.5 mm. The anterior bridge 262 can also have any thickness as needed, but in one embodiment, it can have a thickness of about 10 mm. The load sharing between the opposed sides can minimize the problems associated with completely separate medial and lateral sides, where excessive loading on one side can cause the tibial component 200 to subside into the tibial bone leading to implant failure. Another advantage of the one piece metal base plate 260 is to help avoid errors in relative positioning of separate medial and lateral tibial compartments 220, 210. The anterior bridge 262 of the base plate 260 can be thicker than the medial and lateral compartments 220, 210 for increased strength. Additionally, the anterior surface of the bridge 262 can have a groove 264 to accommodate the patellar tendon, particularly in deep flexion. The knee prosthesis 100 can also be effective to restore a natural tibiofemoral joint line. In standard TKA, the tibial and femoral bone cuts are made perpendicular to the mechanical axis of the leg. This results in a tibiofemoral joint line, which is rotated by about 3 degrees relative to the mechanical axis and that is not restored to normal, as shown in FIG. 18B. In embodiments of the invention, the tibial cut can also be made perpendicular to the mechanical axis.

However, the thicknesses of the medial and lateral tibial compartments 220, 210 differ by about 3-4 mm, with the lateral compartment 210 being thicker than the medial compartment 220. The femoral component 300 can be designed such that when it is mounted at about a 5-6 degree valgus angle relative to the mechanical axis (standard surgical protocol), the condylar surfaces 310, 320 of the TKA femoral component 300 match the normal femoral condylar surfaces. Thus, the femoral and tibial component 300, 200 together can result in an anatomic tibiofemoral joint line.

Figure 18C:
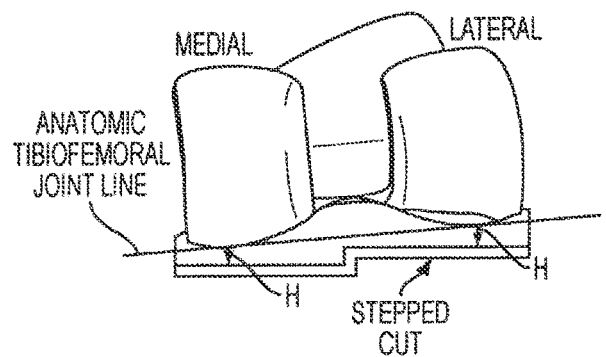
FIG. 18C is an illustration of a stepped cut in bone for an exemplary knee prosthesis.

In another embodiment, it is also possible to have a "stepped" cut on the tibia and a corresponding tibial design where the medial and lateral tibial compartments 220, 210 have the same thickness, but the bottom of the lateral tibial compartment 210 is raised, as shown in FIG. 18C. This would allow for a tibial cut perpendicular to the mechanical axis and an anatomic joint line, while reducing the amount of bone resected from the lateral side of the tibia.

The embodiments described herein can be based directly on 6 degrees-of-freedom in vivo knee kinematics, thus capturing all the complexities of in vivo knee joint motion. Prior art designs have relied on in vitro data obtained from tests on cadaveric knees that are not completely representative of in vivo conditions, and they have incorporated kinematic information corresponding to only 3 out of 6 degrees-of-freedom. Information regarding changes in superior-inferior position of the femur relative to the tibia, medio-lateral position of the femur relative to the tibia, and varus-valgus rotation is not included in these prior designs.

A person skilled in the art will appreciate that a knee prosthesis according to the present invention can be provided in the form of only part of the components described above. For example, in the case of localized disease or trauma, only a tibial component or femoral component may be provided. Similarly, only a single tibial compartment (medial or lateral) or a single femoral condyle (medial or lateral) may be provided.

In some embodiments, various components described herein can be included in a kit. For example, one or more tibial components and one or more femoral components can be included in the kit. One or more of the tibial components can include an ACL ramp and/or a cam for mating with a post on a femoral component. In addition, one or more base plates can be provided for receiving a tibial component.

Figure 19A:
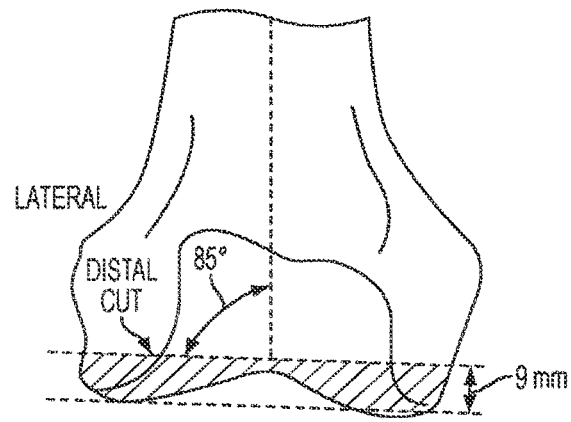
FIG. 19A is a front view of a femur illustrating the bone cut made during standard knee replacement surgery.
Figure 19B:
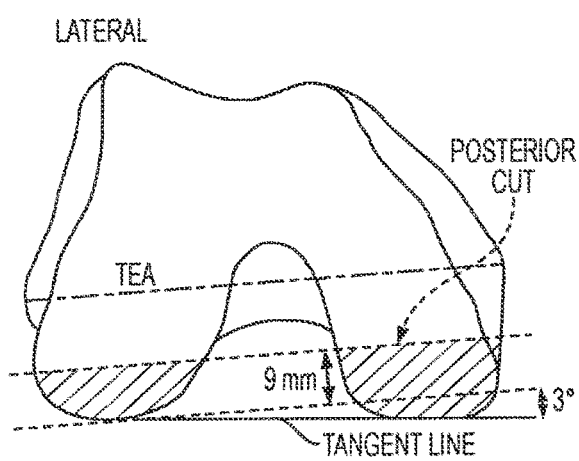
FIG. 19B is another view of femur of FIG. 19A.

The knee prostheses described herein are usable in any surgical procedures now known or yet to be discovered. In some embodiments, a surgical procedure for implanting an exemplary knee prosthesis can include mounting the femoral component. The distal femur can be cut perpendicular to the mechanical axis of the leg, as illustrated in FIG. 18B, which equals about 5 degree to 6 degree valgus angle relative to the axis of the femoral shaft as shown in FIG. 19A. The posterior femur is cut at about 3 degree external rotation relative to a line tangent to the posterior condyles, as shown in an axial view at FIG. 19B. The distal and posterior femoral cuts can be measured relative to the lateral femoral condyle, and can match the thickness of the femoral prosthesis component, usually about 9 mm.

Since the exemplary femoral components described herein can restore the anatomy and joint line of the normal knee, the distal and posterior femoral bone cuts will be made parallel to the joint line with the knee rotated at 0° flexion and 90° flexion, respectively as illustrated in FIG. 18B. Due to the extended superior-posterior arcs on the femoral condyles a modification to the standard bone cutting is required, as shown in FIG. 13A. The first option is to have a thicker posterior bone cut of about 3 mm more. The second option is to have an inclined/inwardly tilted posterior cut of about 10 degrees. This involves cutting less bone than option 1. The third option is to have an additional, superior bone cut (tilted about 45 degrees relative to vertical line). This option involves cutting less bone than options 1 and 2. The final option is to have a smooth contoured bone cut to minimize femoral bone cutting (even less than standard bone cuts), and to make it easier to mount the femoral component.

Figure 19C:
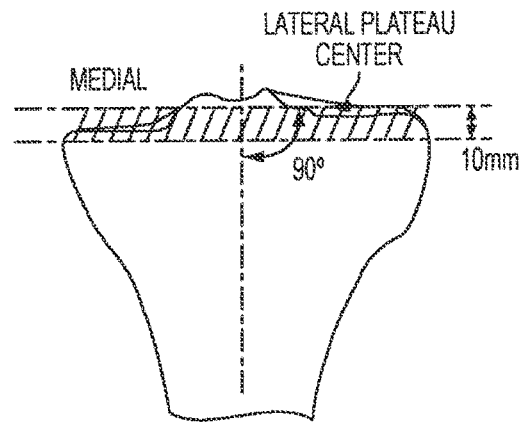
FIG. 19C is a front view of a tibia illustrating the cut made during standard knee replacement surgery.
Figure 19D:
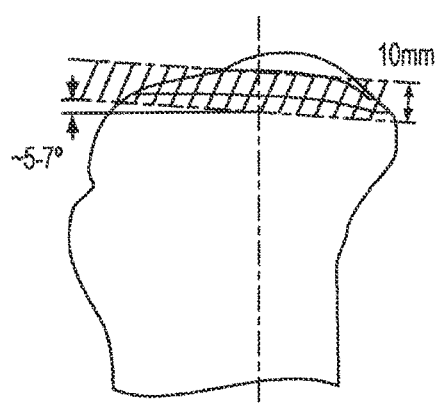
FIG. 19D is a sagittal view of the tibia of FIG. 19C.

In the frontal plane, the tibial bone can be cut perpendicular to the mechanical axis of the leg as illustrated in FIG. 18B, which is approximately the same as cutting perpendicular to the tibial shaft axis. As shown in FIGS. 19C and 19D, the bone cut has about a 5 degree to 7 degree posterior slope in the sagittal plane. The cutting plane is usually located about 10 mm below the surface of the cartilage on the lateral tibial plateau.

It is preferred that device is sterilized. This can be done by any number of ways known to those skilled in the art including beta or gamma radiation, ethylene oxide, steam, and a liquid bath (e.g., cold soak). One skilled in the art will appreciate further features and advantages of the invention based on the above-described embodiments. Accordingly, the invention is not to be limited by what has been particularly shown and described, except as indicated by the appended claims.

All publications and references cited herein are expressly incorporated herein by reference in their entirety.

The invention claimed is:

1. A knee joint prosthesis comprising:
   a tibial component having an inferior surface and a superior surface that serves as a bearing surface for a femoral component, the superior surface having
   a generally concave medial compartment configured to receive and articulate with a medial femoral condyle, and
   a lateral compartment configured to receive and articulate with a lateral femoral condyle, the lateral compartment shape forming a curve in a transverse plane of the tibial component, with a concave side of the curve facing medially and having a length extending from an anterior end thereof to a posterior end thereof,
   wherein the lateral compartment has an anteroposterior profile that is characterized by a first, anterior arc that is concave, a second arc posterior to the first arc that is convex, and wherein an anteroposterior dimension of the second, convex arc of the lateral compartment increases in size from a medial portion of the lateral compartment to a lateral portion of the lateral compartment.

2. The knee joint prosthesis of claim 1, further comprising:
   a medial tibial surface with a concave anterior region having a first length, a convex posterior region having a second length, wherein the first length is different than the second length.

3. The knee joint prosthesis of claim 1, further comprising a femoral component having opposed medial and lateral condyles, each with a bearing surface configured to articulate with the medial and lateral compartments of the tibial component.

4. The knee joint prosthesis of claim 3, wherein the lateral condyle includes a contoured lateral edge configured to allow unimpeded rotation of the lateral condyle about a medial pivot point.

5. The knee joint prosthesis of claim 3, wherein the femoral component includes a trochlear groove disposed between the medial and lateral condyles, the tibial component includes an anterior ramp, and the trochlear groove includes at least two laterally oriented circular arcs having different radii of curvature configured for engaging the anterior ramp of the tibial component.

* * * * *